(12) United States Patent
Fujimaki et al.

(10) Patent No.: US 7,977,656 B2
(45) Date of Patent: Jul. 12, 2011

(54) CHARGED PARTICLE BEAM IRRADIATION SYSTEM AND METHOD OF EXTRACTING CHARGED PARTICLE BEAM

(75) Inventors: Hisataka Fujimaki, Hitachinaka (JP); Satoshi Totake, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 780 days.

(21) Appl. No.: 11/515,920

(22) Filed: Sep. 6, 2006

(65) Prior Publication Data
US 2007/0051905 A1     Mar. 8, 2007

(30) Foreign Application Priority Data

Sep. 7, 2005  (JP) ................................. 2005-258651

(51) Int. Cl.
G21K 5/04    (2006.01)
(52) U.S. Cl. ..................... 250/492.3; 250/505.1; 378/65
(58) Field of Classification Search ................ 250/492.3
See application file for complete search history.

(56) References Cited

U.S. PATENT DOCUMENTS

| | | | |
|---|---|---|---|
| 5,363,008 A | | 11/1994 | Hiramoto et al. |
| 6,034,377 A | * | 3/2000 | Pu ............................ 250/492.3 |
| 7,049,613 B2 | * | 5/2006 | Yanagisawa et al. ...... 250/492.3 |
| 7,122,978 B2 | * | 10/2006 | Nakanishi et al. ............ 315/500 |
| 7,385,203 B2 | * | 6/2008 | Nakayama et al. ........... 250/400 |
| 7,576,342 B2 | | 8/2009 | Hiramoto et al. |
| 2008/0067405 A1 | * | 3/2008 | Nihongi et al. ................ 250/398 |

FOREIGN PATENT DOCUMENTS

| | | |
|---|---|---|
| EP | 1 684 313 A2 | 7/2006 |
| EP | 1 732 369 A2 | 12/2006 |
| EP | 1 733 757 A2 | 12/2006 |
| JP | 2596292 | 1/1997 |
| JP | 11-000408 | 1/1999 |
| JP | 2004-529483 | 9/2004 |
| WO | 02/102123 | 12/2002 |

OTHER PUBLICATIONS

"Instrumentation for treatment of cancer using proton and light-ion beams" W. T. Chu, et al., Rev. Sci. Instrum. 64, (8), Aug. 1993. pp. 2055-2122.

* cited by examiner

*Primary Examiner* — Phillip A. Johnston
(74) *Attorney, Agent, or Firm* — Mattingly & Malur, PC

(57) ABSTRACT

A charged particle beam irradiation system includes an accelerator for accelerating a charged particle beam, a beam irradiation apparatus having a beam energy modulator and arranged for irradiating an object with the charged particle beam extracted from the accelerator and having passed the beam energy modulator, which is rotated and whose thickness in the axial direction differs in the rotational direction, and a controller for controlling the extraction intensity of the charged particle beam extracted from the accelerator, while the charged particle beam is being extracted, on the basis of the rotational angle of the beam energy modulator.

42 Claims, 21 Drawing Sheets

FIG. 7

| IRRADIATION FIELD DIAMETER | RANGE | BEAM ENERGY | SC1 THICKNESS | RANGE SHIFTER THICKNESS | RMW TYPE | SSC TYPE | BEAM EXTRACTION PATTERN |
|---|---|---|---|---|---|---|---|
| φ20 [cm] | 40 [mm] ... 90 [mm] | 100 [MeV] | 2 [mm] | 50 [mm] ... 0 [mm] | 1-A | 1-1 | 1-A-I |
| | 90 [mm] ... 150 [mm] | 150 [MeV] | 4 [mm] | 60 [mm] ... 0 [mm] | | | 1-A-II |
| | | 200 [MeV] | 7 [mm] | 0 [mm] | 1-B | 1-2 | 1-B-I |
| | 150 [mm] | 250 [MeV] | 10 [mm] | 0 [mm] | | | 1-B-II |
| φ6 [cm] | 40 [mm] ... 90 [mm] | 100 [MeV] | 1 [mm] | 50 [mm] ... 0 [mm] | 2-A | 2-1 | 2-A-I |
| | 90 [mm] ... 150 [mm] | 150 [MeV] | 2 [mm] | 60 [mm] ... 0 [mm] | | | 2-A-II |
| | | 200 [MeV] | 3.5 [mm] | 0 [mm] | 2-B | 2-2 | 2-B-I |
| | 150 [mm] | 250 [MeV] | 5 [mm] | 0 [mm] | | | 2-B-II |

FIG. 8

| RMW TYPE | | 1-A | | | 1-B | | | 2-A | | | 2-B | | |
|---|---|---|---|---|---|---|---|---|---|---|---|---|---|
| | | NO.1 | NO.2 | NO.3 | NO.1 | NO.2 | NO.3 | NO.1 | NO.2 | NO.3 | NO.1 | NO.2 | NO.3 |
| SOBP 1cm | OFF | 10.0 | 130.0 | 250.0 | 10.0 | 130.0 | 250.0 | 10.0 | 130.0 | 250.0 | 10.0 | 130.0 | 250.0 |
| | ON | 110.0 | 230.0 | 350.0 | 110.0 | 230.0 | 350.0 | 110.0 | 230.0 | 350.0 | 110.0 | 230.0 | 350.0 |
| SOBP 2cm | OFF | 20.0 | 140.0 | 260.0 | 20.0 | 140.0 | 260.0 | 20.0 | 140.0 | 260.0 | 20.0 | 140.0 | 260.0 |
| | ON | 100.0 | 220.0 | 340.0 | 100.0 | 220.0 | 340.0 | 100.0 | 220.0 | 340.0 | 100.0 | 220.0 | 340.0 |
| SOBP 3cm | OFF | 30.0 | 150.0 | 270.0 | 30.0 | 150.0 | 270.0 | 30.0 | 150.0 | 270.0 | 30.0 | 150.0 | 270.0 |
| | ON | 90.0 | 210.0 | 330.0 | 90.0 | 210.0 | 330.0 | 90.0 | 210.0 | 330.0 | 90.0 | 210.0 | 330.0 |
| .. | OFF | .. | .. | .. | .. | .. | .. | .. | .. | .. | .. | .. | .. |
| | ON | .. | .. | .. | .. | .. | .. | .. | .. | .. | .. | .. | .. |
| SOBP 10cm | OFF | 55.0 | 115.0 | 235.0 | 55.0 | 115.0 | 235.0 | 55.0 | 115.0 | 235.0 | 55.0 | 115.0 | 235.0 |
| | ON | 65.0 | 125.0 | 245.0 | 65.0 | 125.0 | 245.0 | 65.0 | 125.0 | 245.0 | 65.0 | 125.0 | 245.0 |

FIG. 9

| RMW ANGLE | BEAM EXTRACTION PATTERN | | | | | | | |
|---|---|---|---|---|---|---|---|---|
| | 1-A-I | 1-A-II | 1-B-I | 1-B-II | 2-A-I | 2-A-II | 2-B-I | 2-B-II |
| 0° | 100% | 80% | 100% | 80% | 100% | 80% | 100% | 80% |
| 1° | 100% | 85% | 100% | 85% | 100% | 85% | 100% | 85% |
| 2° | 90% | 90% | 90% | 90% | 90% | 90% | 90% | 90% |
| 3° | 80% | 100% | 80% | 100% | 80% | 100% | 80% | 100% |
| 4° | 70% | 100% | 70% | 100% | 70% | 100% | 70% | 100% |
| ‥ | ‥ | ‥ | ‥ | ‥ | ‥ | ‥ | ‥ | ‥ |
| ‥ | ‥ | ‥ | ‥ | ‥ | ‥ | ‥ | ‥ | ‥ |
| 358° | 85% | 95% | 85% | 95% | 85% | 95% | 85% | 95% |
| 359° | 90% | 100% | 90% | 100% | 90% | 100% | 90% | 100% |

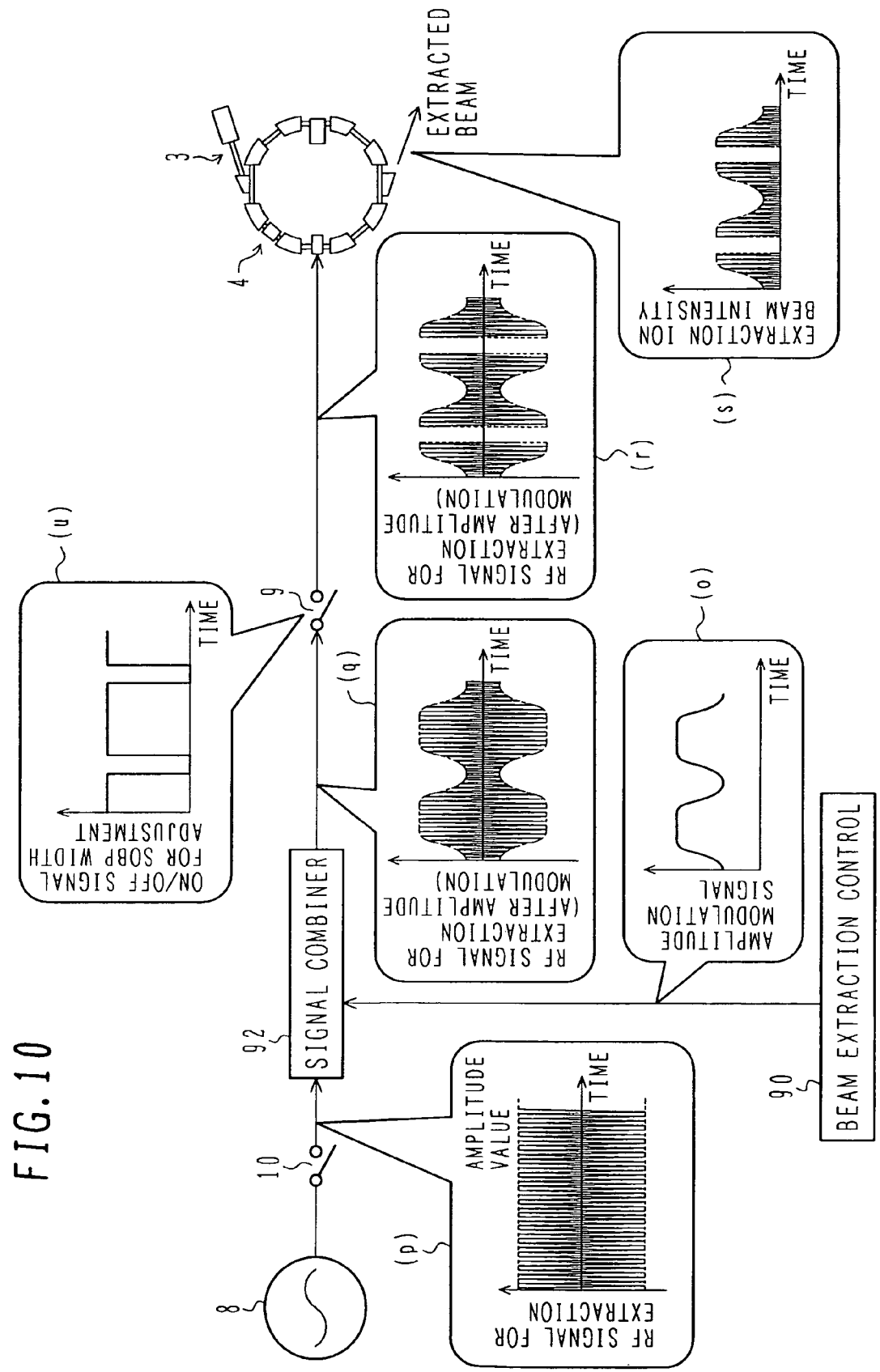

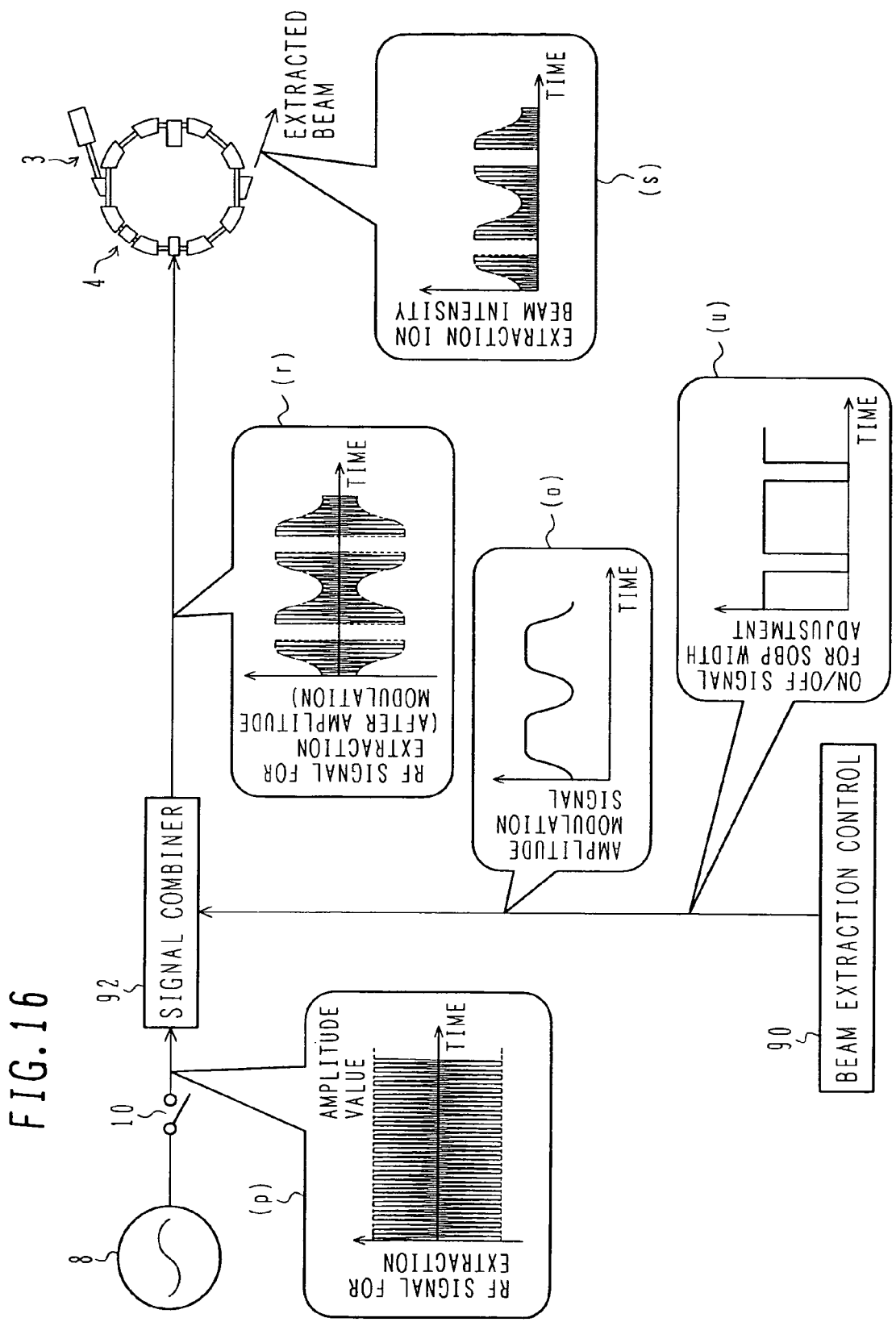

FIG. 20

| RMW ANGLE | BEAM EXTRACTION PATTERN | | | | | | | | |
|---|---|---|---|---|---|---|---|---|---|
| | 1-A-I | 1-A-II | 1-B-I | 1-B-II | 2-A-I | 2-A-II | 2-B-I | 2-B-II |
| 0° | 1 | 1 | 1 | 0 | 1 | 1 | 1 | 1 |
| 1° | 1 | 0 | 0 | 1 | 1 | 1 | 0 | 1 |
| 2° | 0 | 1 | 1 | 0 | 1 | 1 | 0 | 1 |
| 3° | 1 | 0 | 1 | 0 | 0 | 1 | 0 | 0 |
| 4° | 1 | 1 | 1 | 1 | 1 | 0 | 1 | 0 |
| ... | ... | ... | ... | ... | ... | ... | ... | ... |
| ... | ... | ... | ... | ... | ... | ... | ... | ... |
| 358° | 1 | 0 | 1 | 1 | 1 | 1 | 0 | 1 |
| 359° | 1 | 1 | 0 | 1 | 0 | 1 | 1 | 1 |

CHARGED PARTICLE BEAM IRRADIATION SYSTEM AND METHOD OF EXTRACTING CHARGED PARTICLE BEAM

BACKGROUND OF THE INVENTION

1. Field of the Invention

The present invention relates to a charged particle beam irradiation system and a method of extracting a charged particle beam. More specifically, the invention relates to a charged particle beam irradiation system and a method of extracting a charged particle beam that can be suitably applied to a material irradiation apparatus for irradiating a material with a charged particle beam, a food irradiation apparatus for irradiating food with a charged particle beam, and a particle beam therapy system for irradiating an affected part of a body with a charged particle beam, such as a proton or carbon ion beam.

2. Description of the Related Art

There is a known method of cancer treatment in which the affected part of the body of a patient is irradiated with a charged particle beam (ion beam), such as a proton or carbon ion beam. An ion beam irradiation system includes an ion beam generator, a beam transport system, and an irradiation device. The ion beam generator accelerates an ion beam circulating around an orbit to a predetermined energy. An ion beam that is accelerated to the predetermined energy is transported to the irradiation device via the beam transport system and is emitted to an object.

The ion beam generator includes a circular accelerator, such as a synchrotron or a cyclotron. Japanese Patent No. 2,596,292 describes, as an ion beam generator, a circulating unit for circulating an ion beam along an orbit, a radio frequency (RF) applying device for increasing the amplitude of betatron oscillation of an ion beam inside a separatrix in phase space, and an electrostatic deflector for extracting an ion beam from the orbit. The RF applying device increases the amplitude of betatron oscillation of an ion beam stably orbiting inside the synchrotron by applying an RF magnetic field or an RF electric field when the ion beam is accelerated to a predetermined energy inside the synchrotron. An ion beam whose amplitude of betatron oscillation is increased transits outside the separatrix and is extracted from the synchrotron to the beam transport system.

In a particle beam therapy system, an irradiation device extracts an ion beam and emits this ion beam into a patient's body. The ion beam has a physical characteristic in which it deposits most of its energy at the end of its path (i.e., at its Bragg peak). The position in the patient's body where the Bragg peak is generated depends on the energy of the ion beam.

Normally, an affected part of the body of the patient has a certain thickness along the depth direction (i.e., beam progression direction) from the surface of the body. To irradiate the entire thickness of the affected part in the depth direction, the energy of the ion beam has to be controlled to generate a spread-out Bragg peak (SOBP) that is spread out uniformly in the depth direction.

From such a standpoint, a charged particle beam irradiation system including an irradiation device provided with a range modulation wheel (RMW) has been proposed (refer to "Review of Scientific Instruments," Vol. 64, No. 8, August 1993, p. 2,077, FIG. 30). The RMW includes a plurality of blades disposed along the circumferential direction. The longitudinal cross-section of the blades is wedge-shaped such that the thickness of the blades gradually increases or decreases in the axial direction. The RMW is provided in the beam path inside the irradiation device and rotates on a plane orthogonal to the beam path. As the charged particle beam passes through the rotating RMW, the position where the Bragg peak is generated in the patient's body changes periodically. As a result, based on time integration, a SOBP that is relatively spread out from near the surface of the body to inside the body is generated.

JP, A 2004-529483 describes a technology for adjusting the intensity of a proton beam by changing the electrical current supplied to the ion source. More specifically, according to JP, A 2004-529483, to obtain a beam with a predetermined intensity by using a cyclotron, the intensity of an extracted beam is actually measured, and the electrical current supplied to the ion source is control on the basis of the measurement results.

A charged particle beam irradiation apparatus described in JP, A 11-408 includes a pair of filters for absorbing energy. The filters have spiral sections whose thickness in the shaft direction changes in a spiral manner around the center of the shaft. The filters are disposed in an overlapping manner in the beam path and rotate at a constant speed in opposite directions. By turning on and off the ion beam source according to the rotational angles of the filters, the thickness of the overlapping spiral sections where the beam passes through is controlled to shift the depth reached by the beam in the object being irradiated. In this way, the dose distribution in the depth direction of the object can be controlled.

SUMMARY OF THE INVENTION

A beam energy adjuster includes wedge-shaped energy absorbers whose shapes are optimized in accordance with the energy of the extracted ion beam. Since the depth and size of an affected part of the body differs depending on the patient, for a charged particle beam irradiation system used in a medical institution, beam energy adjusters (RMWs) optimized for ion beams having various different energy levels had to be used. These optimized beam energy adjusters have different shapes depending on the irradiation field diameter of an ion beam and the range of an ion beam.

The inventors have carried out a study to seek for a way to reduce the number of beam energy adjusters to be used for ion beams having various different energy levels. As a result, the inventors have discovered that the uniformity of the dose distribution in the depth direction of the body is degraded when an ion beam having an energy level different from the energy level to which the shape of the beam energy adjuster is optimized is incident on the beam energy adjuster.

An object of the present invention is to provide a charged particle beam irradiation system and a method of extracting a charged particle beam for generating a specific dose distribution with a reduced number of energy adjusters.

A charged particle beam irradiation system includes an accelerator for accelerating a charged particle beam, a beam irradiation apparatus having a beam energy modulator and arranged for irradiating an object with the charged particle beam extracted from the accelerator and having passed the beam energy modulator, which is rotated and whose thickness in the axial direction differs in the rotational direction, and a controller for controlling the extraction intensity of the charged particle beam extracted from the accelerator, while the charged particle beam is being extracted, on the basis of the rotational angle of the beam energy modulator.

Even when an ion beam having energy different from the energy to which the shape of the beam energy modulator is optimized is incident on the beam energy modulator, the controller controls the extraction intensity of the charged particle beam extracted from the accelerator is controlled on the basis of the rotational angle of the beam energy modulator. Therefore, the dose distribution within the SOBP width in the depth direction of the body can be uniformized even more. As a result, the number of beam energy modulators required is reduced.

According to the present invention, the number of beam energy adjusters required for a charged particle beam irradiation system for emitting ion beams having various different energy levels and a method for extracting a charged particle beam can be reduced.

BRIEF DESCRIPTION OF THE DRAWINGS

FIG. 7 is a table showing irradiation condition information stored in a storage device;

FIG. 8 is a table showing SOBP width condition information stored in a storage device;

FIG. 9 is a table showing beam extraction intensity condition information stored in a storage device;

FIG. 10 is a block diagram of a particle therapy system according to a preferred embodiment of the present invention and is a schematic view of signals output to control the beam extraction intensity;

FIG. 11A illustrates the change over time in the beam current when the RMW is constantly irradiated with an ion beam with a constant extraction intensity at all rotational angles and FIG. 11B illustrates the change over time in the beam current when the extraction intensity of the ion beam is controlled in accordance with the rotational angle of the RMW;

FIG. 13A illustrates the change over time in the beam current when the RMW is constantly irradiated with an ion beam with a constant extraction intensity at all rotational angles and FIG. 13B illustrates the change over time in the beam current when the extraction intensity of the ion beam is controlled in accordance with the rotational angle of the RMW;

FIG. 15A is a schematic view of the number of RMWs required for a known irradiation method, FIG. 15B is a schematic view of the number of RMWs required when the SOBP width is controlled by starting and stopping beam extraction, and FIG. 15C is a schematic view of the number of RMWs required for the present invention;

FIG. 16 is a block diagram of a particle therapy system according to a preferred embodiment of the present invention and is a schematic view of signals output to control the beam extraction intensity;

FIG. 17A illustrates the change over time in the beam current when the RMW is constantly irradiated with an ion beam with a constant extraction intensity at all rotational angles and FIG. 17B illustrates the change over time in the beam current when the extraction intensity of the ion beam is controlled and the SOBP width is adjusted in accordance with the rotational angle of the RMW;

FIG. 20 is a table showing beam extraction intensity condition information stored in a storage device.

DESCRIPTION OF THE PREFERRED EMBODIMENTS

Embodiments of the present invention will be described with reference to the drawings.

First Embodiment

Figure 1:
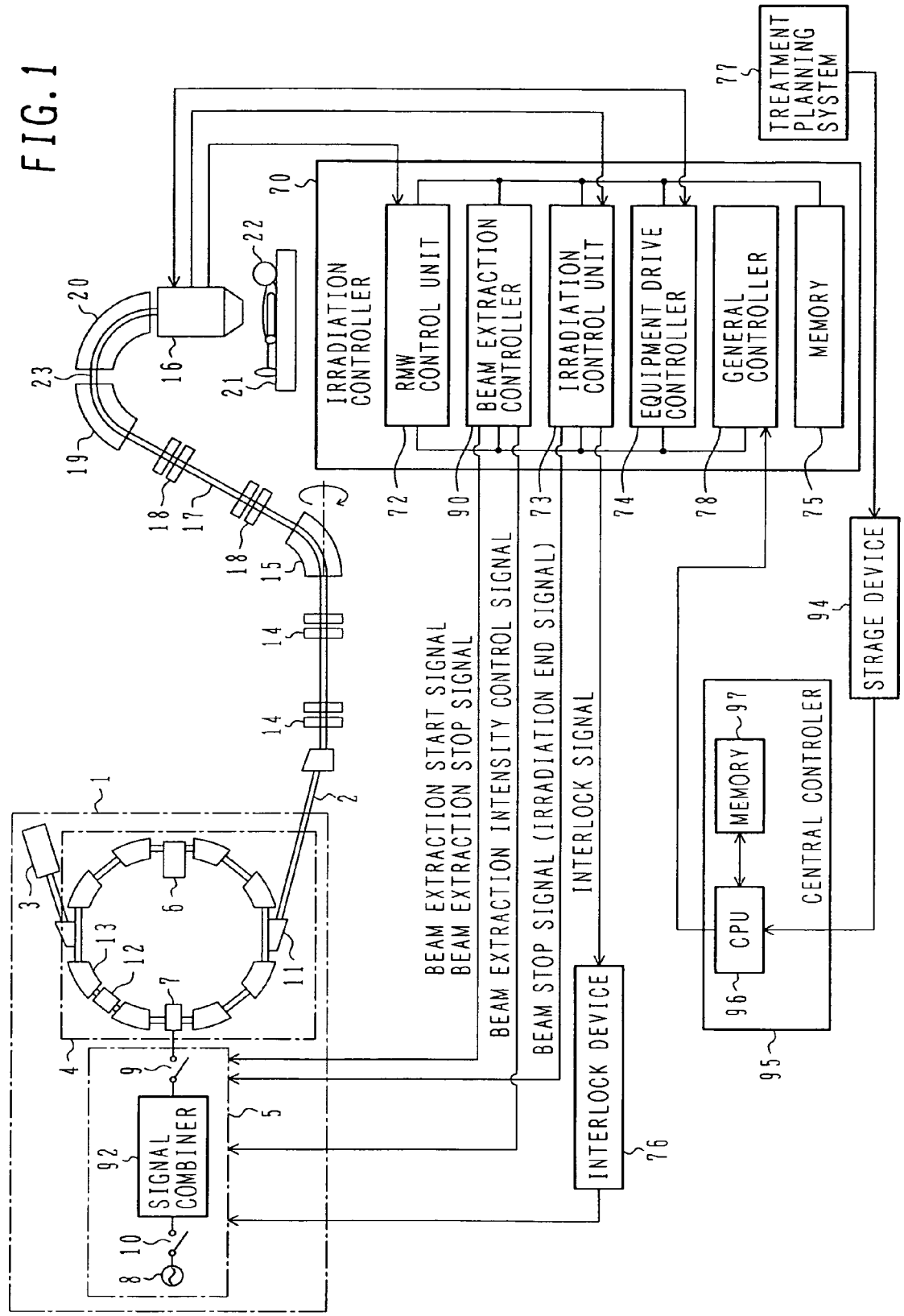
FIG. 1 is an overall schematic view of a particle therapy system according to a preferred embodiment of the present invention.
Figure 2:
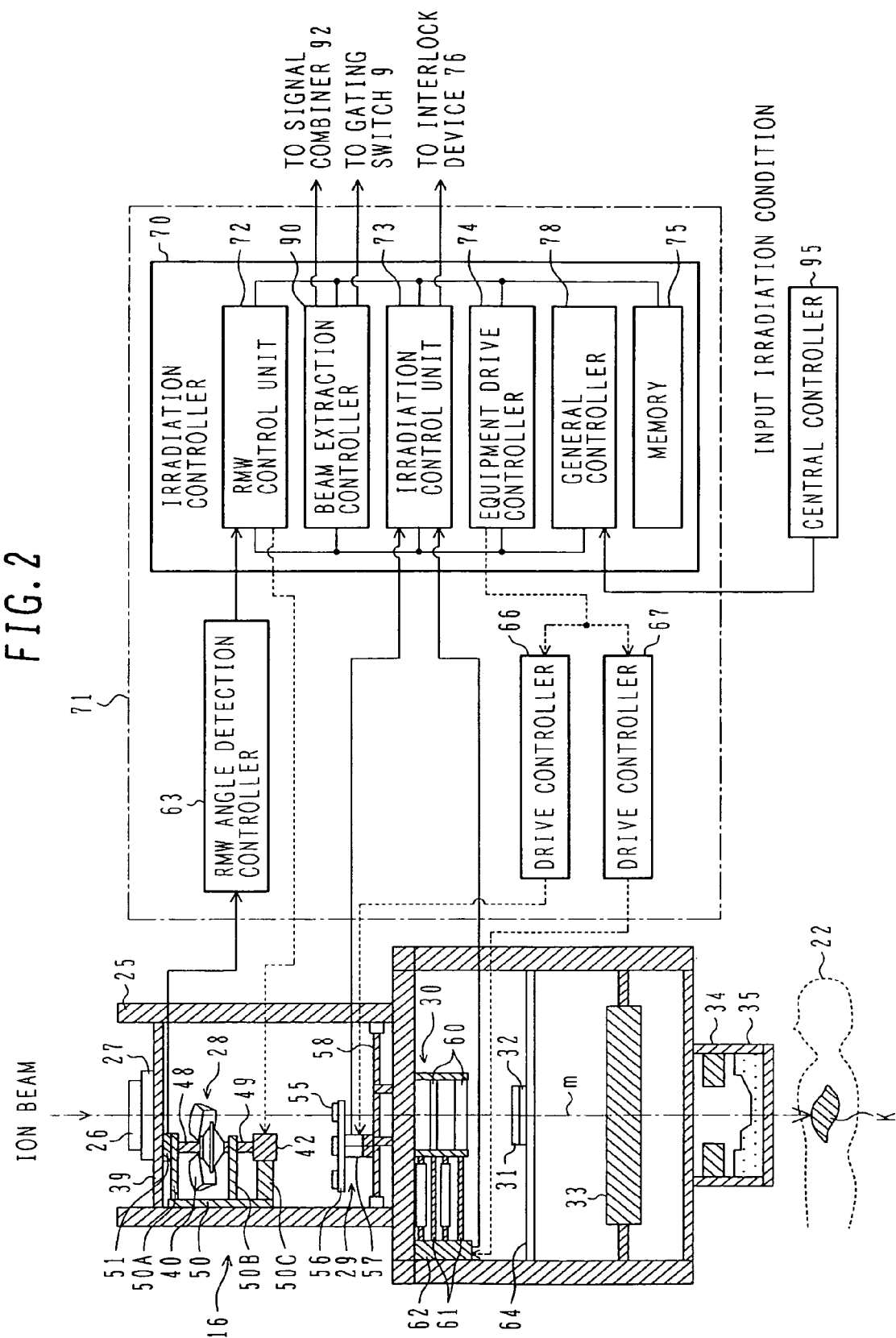
FIG. 2 is a longitudinal cross-sectional view illustrating the structure of an irradiation apparatus included in the particle therapy system according a preferred embodiment of the present invention and is a block diagram of a control system.

A particle beam therapy system that is a charged particle beam irradiation system according to a preferred embodiment of the present invention will be described with reference to FIGS. 1 and 2. The particle beam therapy system according to this embodiment includes an ion beam generator 1, a beam transport system 2, and an irradiation apparatus (ion beam irradiation device) 16 and a control system 71 (refer to FIG. 2). The beam transport system 2 connects the ion beam generator 1 and the irradiation apparatus 16. The control system 71 includes an irradiation controller 70. A treatment planning system 77 is connected to a storage apparatus 94.

The ion beam generator 1 includes an ion source (not shown in the drawings), a pre-accelerator 3, a synchrotron 4, and a radio frequency (RF) applying device 5 for beam extraction. The pre-accelerator 3 is connected to the ion source and the synchrotron 4. The synchrotron 4 includes an RF accelerator cavity 6, a RF applying electrode (RF applying device) 7, an electrostatic deflector 11 for beam extraction, a quadrupole magnet 12, and a bending magnet 13. The RF accelerator cavity 6 is connected to a RF power source (not shown in the drawings) for applying RF power that is different from a RF power source 8, described below. The RF applying electrode 7 is connected to the RF applying device 5 for beam extraction. The RF applying device 5 includes the RF power source 8, a gating devices (gating switches) 9 and 10 and a signal combiner 92. The signal combiner 92 is connected to the RF power source 8 via the gating switch 10. The signal combiner 92 is also connected to the RF applying electrode 7 via the gating switch 9. The electrostatic deflector 11 is connected to the beam transport system 2.

The beam transport system 2 includes a quadrupole magnet 14 and a bending magnet 15. An inversed U-shaped beam path 17 and the irradiation apparatus 16 are mounted on a rotating gantry (not shown in the drawings). The beam transport system 2 is connected to the beam path 17. The beam path 17 includes a quadrupole magnet 18, a bending magnet 19, and a bending magnet 20 in this order from upstream of the beam progression direction. The beam path 17 is connected to the irradiation apparatus 16 disposed in a treatment room.

The inner structure of the irradiation apparatus 16 will be described with reference to FIG. 2. The irradiation apparatus 16 includes a casing 25. The casing 25 is attached to the rotating gantry. Inside the casing 25, in order from upstream of the ion beam progression direction, a beam profile monitor 26, a dose monitor (first dose detection unit) 27, a range modulation wheel (RMW) apparatus 28, a second scatterer 29, a range adjuster (e.g., range shifter) 30, a dose monitor (second dose detection unit) 31, a flatness monitor 32, a block collimator 33, a patient collimator 34, and a bolus 35 are disposed on a beam path (beam axis) m.

The beam profile monitor 26 and the dose monitor 27 are provided on a support table 39. The beam profile monitor 26 is used to confirm whether an ion beam emitted through the beam transport system 2 and from the beam path 17 is incident on the irradiation apparatus 16 at a position aligned with the beam axis m. The dose monitor 27 is used to detect the dose of the ion beam incident on the irradiation apparatus 16.

The RMW apparatus 28 includes a RMW (beam energy distribution adjuster) 40, an RMW support member 50, and a motor 42. The RMW 40 is supported by the RMW support member 50 attached to the inner surface of the casing 25. The RMW support member 50 includes supporting sections 50A and 50B provided opposite to each other in the direction of the beam axis m. Rotary shafts 48 and 49 are rotatably attached to the supporting sections 50A and SOB, respectively. The RMW 40 is interposed between the supporting sections 50A and 50B. The RMW 40 is supported in a manner such that a rotary shaft 43 of the RMW 40 is joined with the rotary shafts 48 and 49. Such a structure allows the RMW 40 to be removed from between the supporting sections 50A and 50B for replacement. The replacement of the RMW 40 can be carried out by an operator. The supporting sections 50A and 50B are provided at positions that do not interfere with the beam path m. A goniometer 51 is provided above the supporting section 50A. The goniometer 51 detects the rotational angle (rotational phase) of the rotary shaft 48 (i.e., RMW 40). The supporting section 50B is provided with the rotary shaft 49. The rotary shaft 49 is connected to the motor 42 that is held by a supporting section 50C. The motor 42 rotationally drives the RMW 40.

Figure 3:
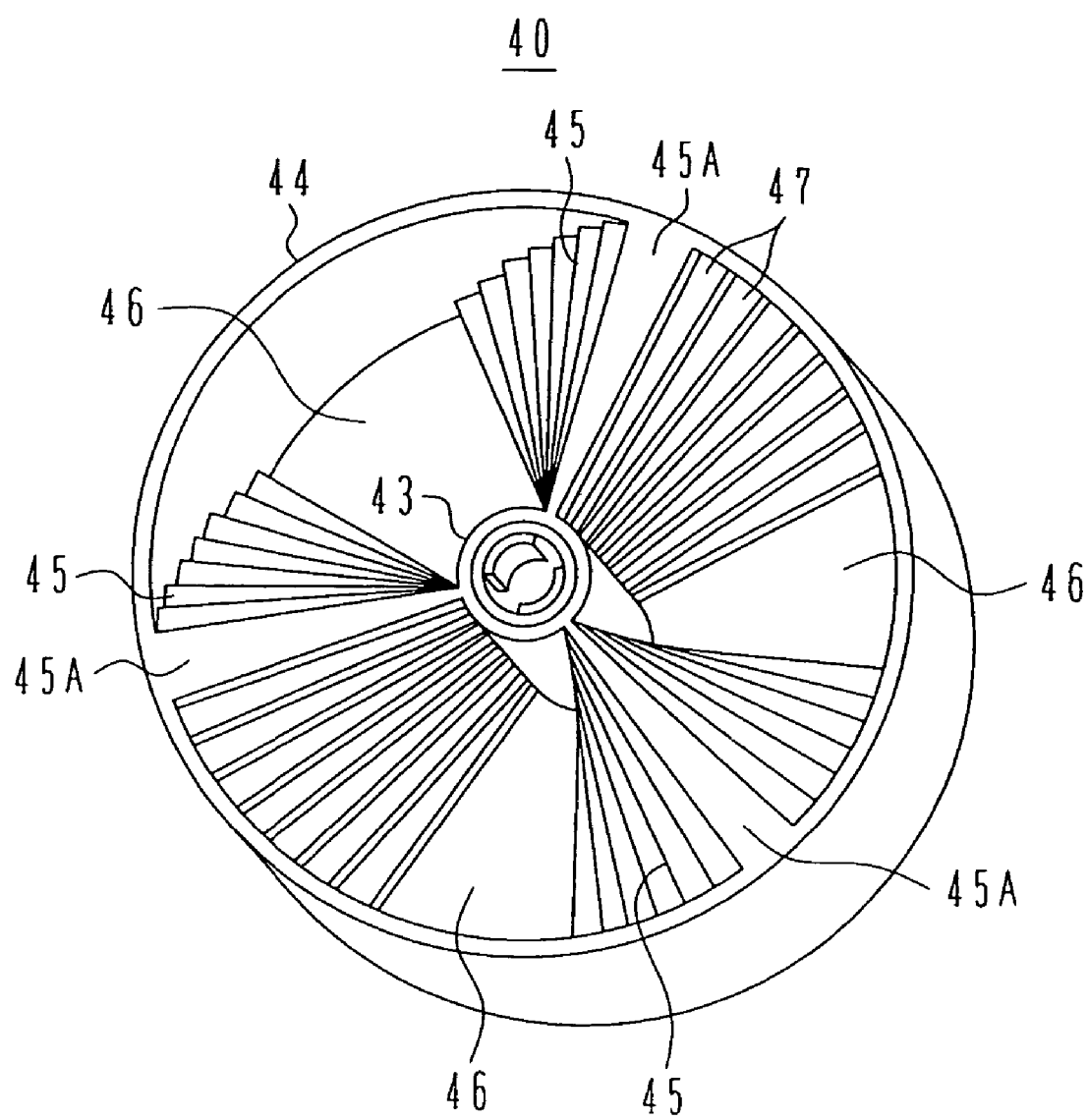
FIG. 3 is a plan view of a RMW.

The detailed structure of the RMW 40 is illustrated in FIG. 3. The RMW 40 includes the rotary shaft 43, a cylindrical member 44 disposed concentrically with the rotary shaft 43, and a plurality of blades 45 (three blades in this embodiment) that are attached to the rotary shaft 43 in a such manner that they extend in the radial direction of the RMW 40. The width of the blades 45 increases outwards in the radial direction (i.e., the cylindrical member 44 side of the blades 45 is wider than the rotary shaft 43 side). The outer edges of the blades 45 in radial direction are attached to the inner surface of the cylindrical member 44. Openings 46 are provided between the blades 45 in the circumferential direction of the RMW 40. In other words, one RMW 40 has three blades 45 and three openings 46 provided between the blades 45. A first scatterer (not shown in the drawing) is provided integrally with the RMW 40. For example, the first scatterer may be provided on the RMW 40 in all areas on which the ion beam is incident. In this embodiment, the RMW 40 and the first scatterer are provided integrally. Instead, however, the first scatterer and the RMW apparatus 28 may be provided separately. The RMW apparatus 28 may include a compensator to compensate for the difference in scattering due to the thickness distribution of the RMW 40 (i.e., due to the difference in the thickness of the flat sections of the RMW 40).

Each of the blades 45 has a plurality of flat sections 47 arranged in a stair-like manner along the circumferential direction of the RMW 40 (i.e., the flat sections 47 are equivalent to the flat surfaces of stairs, where one places their foot when climbing the stairs). The distances, in the direction of the beam axis m, from the bottom surface of the RMW 40 to the flat sections 47 differ (i.e., the levels of the flat section 47 differ with respect to the bottom surface of the RMW 40). The thickness of each flat section 47 is referred to as the "flat section thickness." The blades 45 are structured so that the flat section thicknesses of the flat sections 47 increase in the circumferential direction from the openings 46 provided on both sides of the blade 45 toward a blade apex 45A, where the thickness in the direction of the beam axis m of the blade 45 is the greatest. The flat sections 47 each extend from the rotary shaft 43 toward the cylindrical member 44. The width of each flat section 47 in the circumferential direction increases toward the outside in the radial direction.

The second scatterer 29 includes a plurality of second scatterers 55, a rotary table 56, and a motor 57. The motor 57 is disposed on a support member 58 attached to the inner surface of the casing 25. The second scatterers 55 are provided on the rotary table 56 along the circumferential direction. When the rotary table 56 is rotated by the motor 57, a predetermined second scatterer 55 is disposed in the beam path m.

An energy range adjuster 30 includes energy absorbers 60 (four energy absorbers 60 in this embodiment) each having different thicknesses and energy absorber operating devices 61. For example, one energy absorber operating device 61, which is moved by compressed air, is provided for each of the energy absorbers 60. The energy absorber operating device 61 is moved by an energy absorber driving device 62. The energy range adjuster 30 adjusts the depth reached by the ion beam according to the maximum depth of an affected part K of the body of a patient 22.

The dose monitor 31 and the flatness monitor 32 are provided on a support table 64. The dose monitor 31 detects the dose of an ion beam that has passed through the RMW apparatus 28, the second scatterer 29, and the energy range adjuster 30. The flatness monitor 32 determines the flatness (i.e., dose uniformity) in a direction orthogonal to the beam axis m of the ion beam scattered by the RMW 40 (more specifically the scatterers provided on the RMW 40) and the second scatterers 55.

The block collimator 33 has an opening for coarsely shaping the irradiation field of an ion beam on a plane orthogonal to the beam axis m. Components of the ion beam incident on the block collimator 33 outside the opening are blocked. The patient collimator 34 shapes the ion beam more finely to match the shape of the ion beam with shape of the affected part K of the body of the patient 22 (for example, the shape of the cancerous or tumorous part of the body). The bolus 35 adjusts the range at each position on a plane orthogonal to the beam axis m according to the depth and shape of the affected part K that is the target to be irradiated.

A central controller 95 includes a central processing unit (CPU) 96 and a memory 97 connected to the CPU 96. The CPU 96 is connected to a storage device 94 and a general control unit 78 of an irradiation controller 70.

A control system 71 (refer to FIG. 2) includes the irradiation controller 70, an RMW angle detection controller 63, a drive controller 66, and a drive controller 67. The irradiation controller 70 includes an RMW control unit 72 (first controlling unit, including a computing unit), a beam extraction intensity controlling unit (beam extraction intensity controller) 90, an irradiation controlling unit 73 (second controlling unit), an equipment drive controller 74, and a memory 75. The memory 75 is connected to the RMW control unit 72, the beam extraction intensity controller 90, the irradiation controlling unit 73, and the equipment drive controller 74. The RMW control unit 72 is connected to the RMW angle detection controller 63 and the motor 42. The beam extraction intensity controller 90 is connected to the signal combiner 92 (refer to FIG. 1) and the gating switch 9 (refer to FIG. 1). The RMW angle detection controller 63 is connected to the goniometer 51. The irradiation controlling unit 73 is connected to the motor 57, the energy absorber operating device 61, and an interlock device 76 (refer to FIG. 1). The equipment drive controller 74 is connected to the drive controller 66 and the drive controller 67. The drive controller 66 is connected to the motor 57. The drive controller 67 is connected to the energy absorber operating device 61.

According to this embodiment, the control system 71 includes the irradiation controller 70, the RMW angle detection controller 63, and the drive controllers 66 and 67. However, the control system 71 may be configured so that it is capable of functioning as the irradiation controller 70, the RMW angle detection controller 63, and the drive controllers 66 and 67.

Next, information that is stored in the memory 75 will be described. The memory 75 stores the information shown in FIGS. 7, 8, and 9.

As shown in FIG. 7, the memory 75 stores information on irradiation field diameter, range, beam energy, first scatterer (SC1) width, range shifter thickness, RMW type, second scatterers (SSC) type, and beam extraction pattern. "Beam energy" is the energy of an ion beam extracted from the synchrotron 4 when acceleration is terminated by the synchrotron 4. If the irradiation field diameter, the beam energy, and the range are determined, by using the information shown in FIG. 7, the corresponding SC1 width, RMW type, SSC type, and beam extraction pattern can be determined. Then, the range shifter thickness corresponding to the range can be determined. More specifically, if the irradiation field diameter is 20 cm, the beam energy is 100 MeV, and the range is 40 mm, the range shifter thickness will be 50 mm, the SSC type will be 1-1, the RMW type will be 1-A, which is a RMW having a first scatterer with a scatterer (SC) thickness of 2 mm, and the beam extraction pattern will be 1-A-I. Information on the SC1 width, range shifter thickness, RMW type, SSC type and beam extraction pattern corresponding to the irradiation field diameter, the beam energy, and the range is obtained in advance by calculation and experimentation. The irradiation field diameter, the beam energy, and the range are included in treatment plan information determined when carrying out treatment planning.

As shown in FIG. 8, the memory 75 stores information on the rotational angle of the RMW 40 that extracts an ion beam (beam extraction information) and information on the rotational angle of the RMW 40 for stopping the ion beam extraction (beam start/stop control angle information) that correspond to the SOBP width and the type of the RMW 40. If the SOBP width and the type of the RMW 40 are determined, by using the information shown in FIG. 8, information on where (which area) to start and stop extraction of the beam (beam start/stop control angle information) can be obtained. More specifically, if the SOBP width is 1 cm and the type of the selected RMW is 1-A, the ion beam extraction is stopped when the rotational angles of the RMW 40 are 10.0°, 130.0°, or 250.0°, and the ion beam is extracted when the rotational angle of the RMW 40 is 110.0°, 230.0°, or 350.0°. The rotational angles of the RMW 40 for stopping and starting beam extraction corresponding to the SOBP width and the type of the RMW 40 are obtained in advance by calculation and experimentation.

As shown in FIG. 9, the memory 75 stores information on the relationship between set values of the RMW rotational angle and beam extraction patterns. If the beam extraction pattern is determined, by using the information shown in FIG. 9, the beam extraction intensity corresponding to a rotational angle of the RMW (i.e., the intensity of the ion beam extracted from the synchrotron) can be determined. More specifically, if the beam extraction pattern determined on the basis of the irradiation field diameter and the beam energy is 1-A-I, the set value of the beam extraction intensity is 100% when the set value of the RMW rotational angle is 0°, 90% when 2°, 80% when 3°, 70% when 4°, and so on. The relationship between the rotational angles of the RMW and the beam extraction patterns is determined in advance by calculation and experimentation. According to this embodiment, the information stored in the memory 75, as shown in FIG. 9, includes beam extraction intensities for every 1° of the RMW rotational angle. However, the angular step is not limited to 1° and should be determined on the basis of the accuracy of adjusting the beam extraction intensity that is required for adjusting the dose distribution.

A doctor inputs patient information (i.e., the position and size of the affected part of the body, the irradiation direction of the ion beam, and the maximum irradiation depth) to the treatment planning system 77. The treatment planning system 77 uses treatment planning software to calculate the beam energy, the range of the ion beam, the SOBP width, and the irradiation field diameter, which are all included in the treatment plan information, on the basis of the input information such as the position and size of the affected part of the body. Such treatment plan information is stored in the storage device 94. The CPU 96 of the central controller 95 reads out the treatment plan information from the storage device 94. Then, the treatment plan information is stored in the memory 97 and in the memory 75 through the general control unit 78 of the irradiation controller 70.

The general control unit 78 selects irradiation conditions, such as the thickness of the energy absorbers 60 (range shifter thickness), the type of the RMW 40 (including SC thickness), the type of the second scatterers 55 (SSC type), and the beam extraction pattern, on the basis of the treatment plan information (i.e., beam energy, range of ion beam, SOBP width, and irradiation field diameter). The selected irradiation conditions, i.e., information on the SC1 width, range shifter thickness, RMW type, SSC type, and beam extraction pattern, are stored in the memory 75.

The selected irradiation conditions are displayed on a display unit (not shown in the drawings) that is installed in a control room in the treatment room where preparation of the treatment is carried out. A radiological technologist checks the display screen and installs the RMW 40 indicated on the screen to the irradiation apparatus 16. Then, the rotary shaft 49 of the motor 42 is connected to the rotary shaft 49 of the RMW 40.

The general control unit 78 outputs information on the type of the second scatterer (SSC type) and information on the thickness of the energy absorbers 60 (information on range shifter thickness) that are read out from the memory 75 to the equipment drive controller 74. The equipment drive controller 74 outputs a second scatterer identification signal corresponding to the input type of the second scatterers 55 to the drive controller 66. The drive controller 66 drives the motor 57 on the basis of the second scatterer identification signal so as to rotate the rotary table 56 and dispose the selected second scatterers 55 on the beam axis m.

The drive controller 67 operates the energy absorber operating device 61 via the energy absorber driving device 62 on the basis of the information on the range shifter thickness input through the equipment drive controller 74 so as to move the corresponding energy absorber 60 to a position on the beam axis m.

The drive controllers 66 and 67 send equipment condition information corresponding to the second scatterer 29 and the energy range adjuster 30 to the irradiation controlling unit 73. The irradiation controlling unit 73 reads out the type of the second scatterer selected at the general control unit 78 and the information on the thickness of the absorber from the memory 75 and compares this information to the equipment condition information. If the equipment condition information does not match the type of the second scatterer to be selected and the information on the thickness of the absorber, the irradiation controlling unit 73 sends an interlock signal to the interlock device 76. The interlock device 76 opens the gating switch 10 to interlock the synchrotron 4 so that an ion beam is not extracted from the synchrotron 4. When the equipment condition information matches, the interlock device 76 maintains the closed state of the gating switch 10.

A treatment couch (bed) 21 where the patient 22 is lying is moved so that the affected part K of the body of the patient 22 is aligned with the beam axis m. An accelerator and a transport system controller (not shown in the drawings) receive control signals from the central controller 95 and excite the magnets of the synchrotron 4 and beam transport system 2. After preparation for ion beam extraction is completed, the general control unit 78 sends a RMW rotation control signal to the RMW control unit 72. The RMW control unit 72 outputs a rotation command based on the control signal to drive the motor 42. As a result, the RMW 40 rotates in the direction indicated by an arrow in FIG. 4. The doctor operates an operating panel in the control room to send a treatment start signal to the CPU 96 of the central controller 95. The CPU 96 receives the treatment start signal and starts up the ion source (not shown in the drawings). Ions generated at the ion source (for example, protons or carbon ions) are extracted to the pre-accelerator (liner accelerator) 3.

The synchrotron 4 further accelerates the ion beam (charged particle beam or particle beam) from the pre-accelerator 3. The ion beam is accelerated by applying radio frequency from an RF power source to the RF accelerator cavity 6. The orbiting ion beam is accelerated to reach specific beam energy. Then, an radio frequency is applied by the RF applying electrode 7 to extract the ion beam from the synchrotron 4.

The ion beam extracted from the synchrotron 4 reaches the irradiation apparatus 16 through the electrostatic deflector 11, the beam transport system 2, and the beam path 17. The ion beam is transported through the irradiation apparatus 16 along the beam axis m and is incident on the affected part K of the body. More specifically, the ion beam passes through equipment on the beam axis m including the beam profile monitor 26, the dose monitor 27, the RMW 40, the first scatterer provided on the RMW 40, and the second scatterer 55. The beam size of the ion beam is increased by the first scatterer in a direction orthogonal to the beam axis m. The dose distribution of the ion beam is flattened in this orthogonal direction by the second scatterer 55. The energy absorbers 60 adjust the range of the ion beam inside the body.

The dose of the ion beam is detected by the dose monitor 31, and the flatness of the dose distribution of the ion beam in a direction orthogonal to the beam axis m is confirmed by the flatness monitor 32. Components of the ion beam incident on positions outside the opening of the patient collimator 34 are blocked by the patient collimator 34. The components of the ion beam that pass through the opening of the patient collimator 34 are further transmitted to pass through the bolus 35. The ion beam that has passed through the bolus 35 forms a high-dose region concentrated in a region corresponding to the affected part K of the body and is emitted to the affected part K. When the dose measured by the dose monitors 27 and 31 reach a predetermined dose value, the irradiation controlling unit 73 outputs a beam extraction stop signal, and the gating switch 9 is opened. In this way, ion beam emission to the patient 22 is terminated.

The particle beam therapy system according to this embodiment is capable of controlling the starting and stopping of ion beam extraction from the synchrotron 4 on the basis of the rotational angle of the RMW 40. In this way, various different SOBP widths can be generated using a single RMW 40. This function in addition to other controls by the beam extraction intensity controller 90 will be described below in detail.

The general control unit 78 inputs treatment plan information including irradiation field diameter, range, beam energy, and SOBP width to the beam extraction intensity controller 90. The beam extraction intensity controller 90 selects the type of RMW (for example, 1-A) and information on the beam extraction pattern (for example, 1-A-I) from the information, which is shown in FIG. 7 and stored in the memory 75, on the basis of the irradiation field diameter, range, and beam energy. The beam extraction intensity controller 90 also selects a set value for the rotational angle of the RMW 40 at which ion beam extraction is to be started (turned on) (hereinafter, this set value is referred to as an "ON set value") and the rotational angle set value of the RMW 40 for turning off ion beam extraction (referred to as an "OFF set value") from the information stored in the memory 75, as shown in FIG. 8, on the basis of the SOBP information (for example, SOBP width 1 cm) and the information on the RMW type (for example, 1-A). Moreover, the beam extraction intensity controller 90 selects a set value for beam extraction intensity (for example, 100%, 90%, 80%, or so on) corresponding to the rotational angle from the information stored in the memory 75, as shown in FIG. 9, on the basis of extraction pattern information (for example, 1-A-I).

First, the control for starting and stopping ion beam extraction (i.e., ON and OFF control) by the beam extraction intensity controller 90 will be described. The goniometer 51 detects the rational angle (rotational phase) of the rotating rotary shaft 48, and outputs a corresponding rotational angle detection signal (also referred to as a "rotational angle measurement value") to the RMW angle detection controller 63. The RMW angle detection controller 63 determines the rotational angle of the RMW 40 from the input detection signal and outputs the information on the rotational angle to the beam extraction intensity controller 90. When the input rotational angle measurement value equals the ON set value, the beam extraction intensity controller 90 closes the gating switch 9 by outputting a beam extraction start signal. Since the gating switch 10 is already closed, by closing the gating switch 9, the RF power source 8 is electrically connected to the RF applying electrode 7. In other words, an RF signal from the RF power source 8 is applied to the RF applying electrode 7 via the gating switches 9 and 10. In this way, at the synchrotron 4, an ion beam orbiting inside the separatrix in phase space transits outside the separatrix and is extracted from the synchrotron 4 via the electrostatic deflector 11.

When the rotational angle measurement value equals the OFF set value, the beam extraction intensity controller 90 outputs a beam extraction stop signal to open the gating switch 9. As a result, the application of an RF signal to the RF applying electrode 7 is terminated, and the ion beam extraction from the synchrotron 4 is terminated.

The width of the SOBP generated inside the body of the patient 22 depends on the rotational angles of the RMW 40 for starting and stopping ion beam extraction (i.e., outputting a beam extraction start signal and a beam extraction stop signal). The various widths of the SOBP generated at different rotational angles of the RMW 40 will be described with reference to FIGS. 4, 5, and 6.

Figure 4:
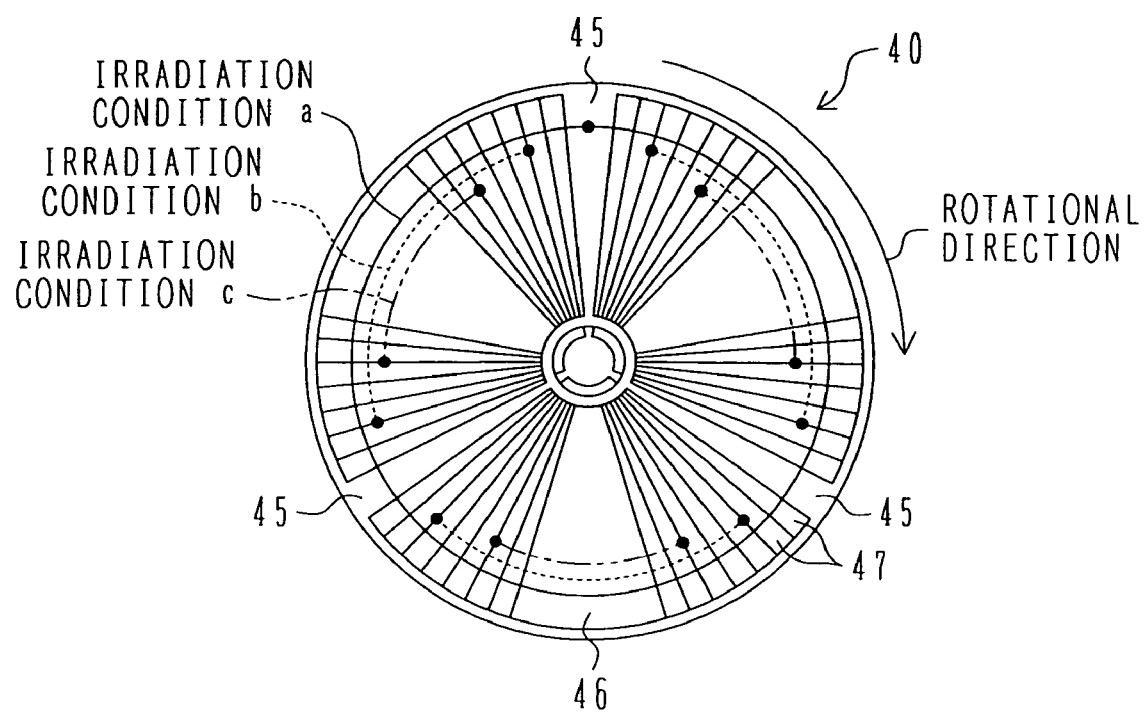
FIG. 4 is a plan view of a RMW illustrating three different ion beam irradiation conditions.
Figure 5:
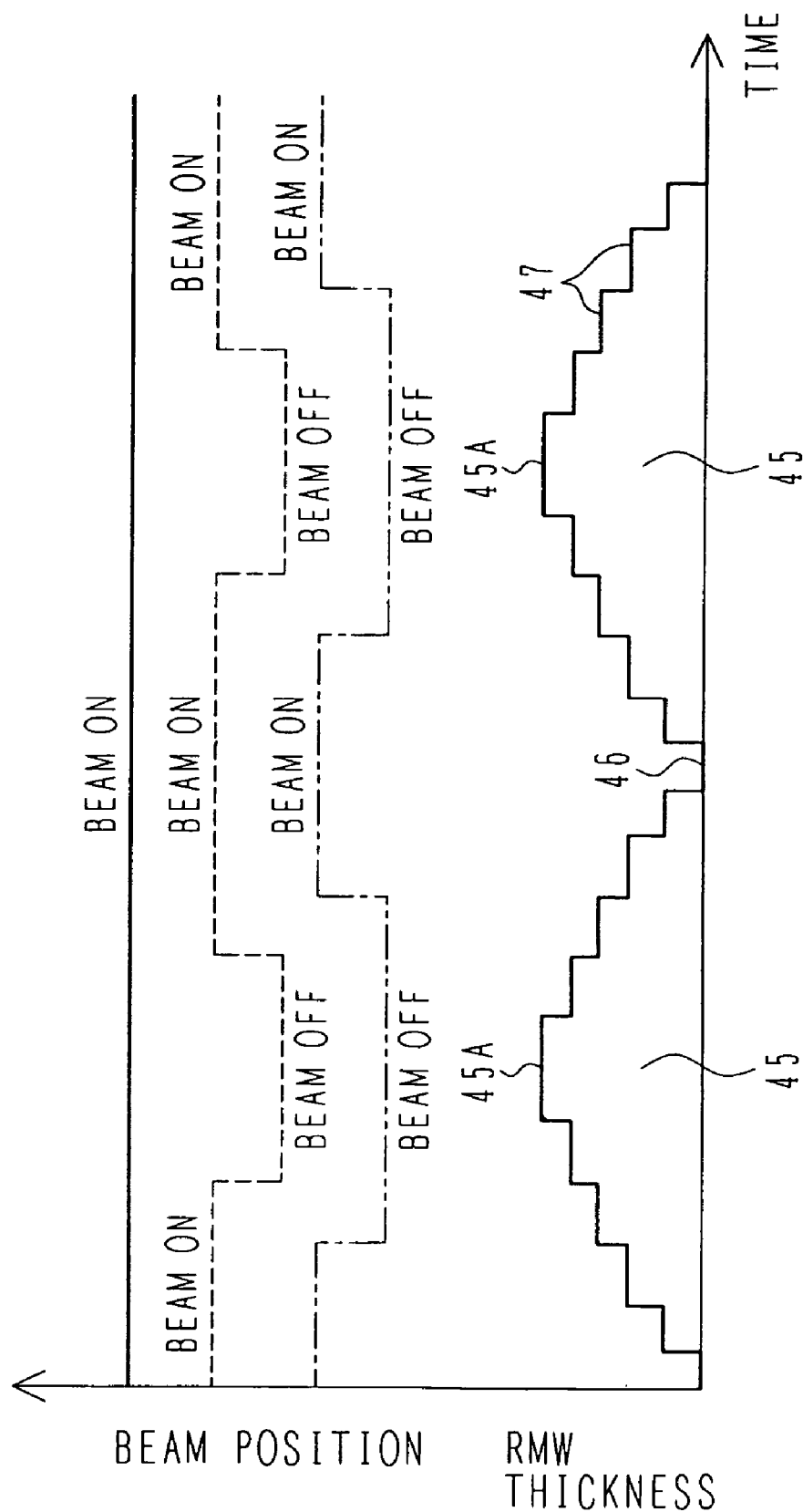
FIG. 5 illustrates the three ion beam irradiation conditions shown in FIG. 4 in time sequence.
Figure 6:
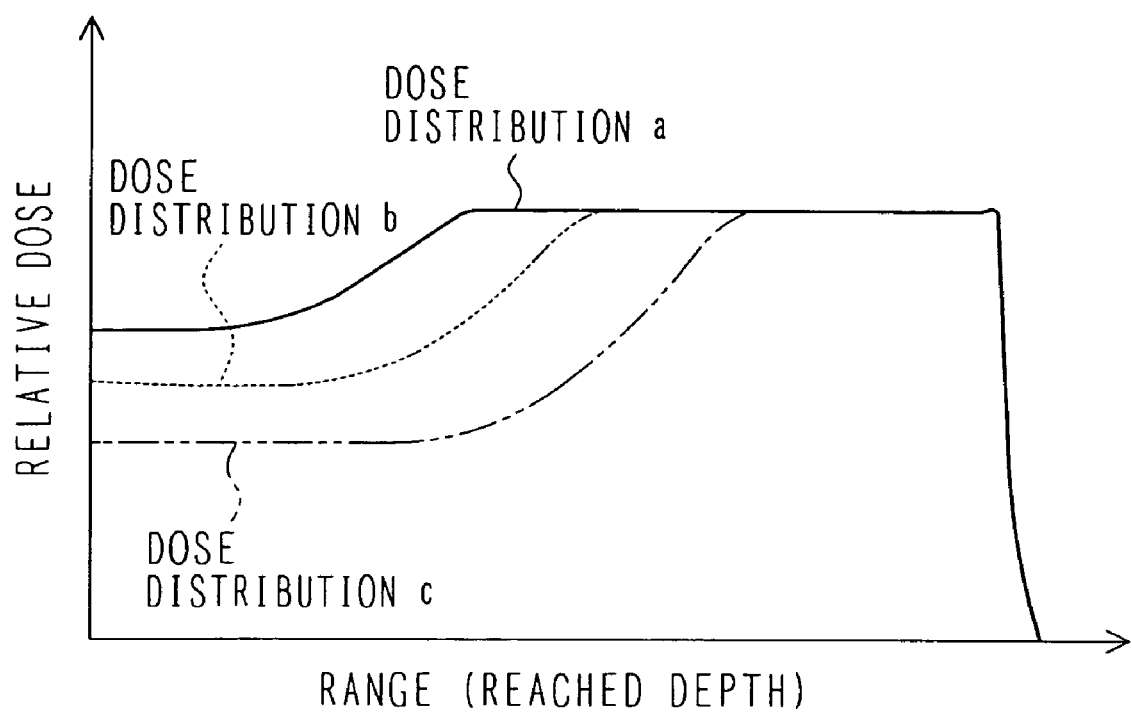
FIG. 6 illustrates dose distributions obtained by the three ion beam irradiation conditions shown in FIG. 4.

FIG. 4 is a plan view of the RMW 40 and illustrates three example irradiation conditions a, b, and c for ion beams. FIG. 5 illustrates these beam irradiation conditions a, b, and c in time series. FIG. 6 illustrates the dose distribution obtained by the irradiation conditions a, b, and c.

In other words, when an ion beam passes through the openings 46 of the RMW 40, the Bragg peak is generated deep inside the body because the energy of the beam is not attenuated. When an ion beam passes through the flat section 47 where the thickness of the blades 45 of the RMW 40 is relatively small, the energy of the beam is slightly attenuated. As a result, the Bragg peak is generated in substantially the middle area of the body. When an ion beam passes through the flat section 47 where the thickness of the blades 45 of the RMW 40 is relatively great, the energy of the beam is greatly attenuated. As a result, the Bragg peak is generated at a shallow area in the body, i.e., close to the surface of the body. Therefore, when the entire circumference of the RMW 40 is irradiated with an ion beam, in a manner such as that represented by the irradiation condition a in FIG. 4, the position of the Bragg peak periodically changes as the RMW 40 is rotated. Consequently, based on time integration, a wide SOBP width that covers an area from near the surface of the body to deep inside the body is obtained, as indicated by the dose distribution a in FIG. 6.

As for the irradiation condition b shown in FIG. 4, ion beam extraction is stopped so that the flat sections 47 (near the blade apex 45A) where the thickness of the blades 45 is relatively great is not irradiated with the ion beam but the other areas around the circumference are irradiated. Therefore, the energy of the ion beam is not greatly attenuated and, thus, the Bragg peak is not generated near the surface of the body. As a result, the SOBP width is smaller for the dose distribution b, shown in FIG. 6, than that of the dose distribution a.

As for the irradiation condition c shown in FIG. 4, the flat sections 47 where the thickness of the blades 45 is relatively small and the openings 46 are irradiated with an ion beam but the other areas around the circumference are not irradiated. Therefore, the energy of the ion beam is not attenuated very much and the Bragg peak is generated deep inside the body. As a result, the SOBP width is smaller for the dose distribution c, shown in FIG. 6, than that of the dose distribution b. As described above, the particle beam therapy system according to this embodiment is capable of generating Bragg peaks having various different SOBP widths using a single RMW 40 by controlling the starting and stopping of the beam extraction according to the rotational angles of the RMW 40.

Next, the control for adjusting the intensity of an ion beam extracted from the synchrotron 4 to adjust the uniformity of the dose distribution in the beam progression direction (i.e., depth direction) while the ion beam is being extracted (i.e., during the ion beam extraction period).

The beam extraction intensity controller 90 controls the intensity of the ion beam extracted from the synchrotron 4 on the basis of a set value of the beam extraction intensity corresponding to a set value of the rotational angle when the input rotational angle measurement value equals a rotational angle measurement value shown in FIG. 9. In other words, as shown in FIG. 10, the beam extraction intensity controller 90 generates an amplitude modulation signal (ion beam extraction intensity control signal (FIG. 10O)) and outputs this amplitude modulation signal to the signal combiner 92. An RF signal (FIG. 10P) that is a carrier wave output from the RF power source 8 is input to the signal combiner 92 via the gating switch 10. The signal combiner 92 combines the RF signal and the amplitude modulation signal and outputs an RF signal for extraction (FIG. 10Q) having modulated amplitude. This RF signal for extraction is an RF signal whose amplitude continuously changes over time and is applied to the RF applying electrode 7 via the gating switch 9. FIG. 10R illustrates the actual RF signal for extraction applied to the RF applying electrode 7 by turning on and off the gating switch 9. The intensity of the ion beam transited outside the separatrix depends on the amplitude of the RF signal for exaction applied to the ion beam orbiting inside the separatrix in phase space. FIG. 10S illustrates the change in the intensity of the ion beam extracted from the synchrotron 4. More specifically, when the amplitude of the RF signal for extraction is great, the intensity of the ion beam extracted from the synchrotron 4 is high, whereas when the amplitude of the RF signal for extraction is low, the intensity of the ion beam extracted from the synchrotron 4 is small. FIG. 10U illustrates a beam extraction ON/OFF signal, i.e., a beam extraction start signal for raising the voltage applied for opening and closing the gating switch 9 to a set voltage and a beam extraction stop signal applied for lowering the voltage below the set value.

Figure 11A:
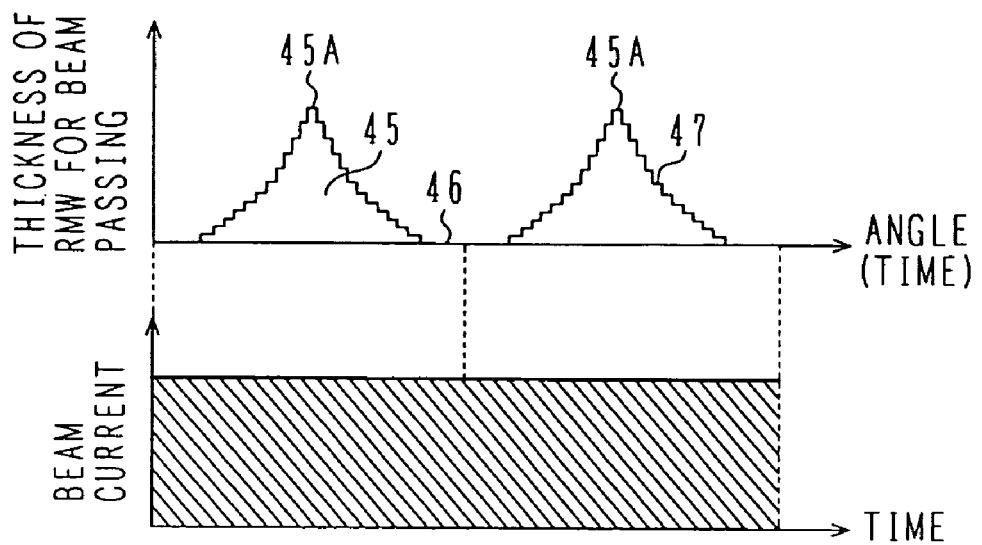
FIGS. 11A and 11B illustrate the relationship between the ion beam extraction intensity and the RMW angle, where
Figure 11B:
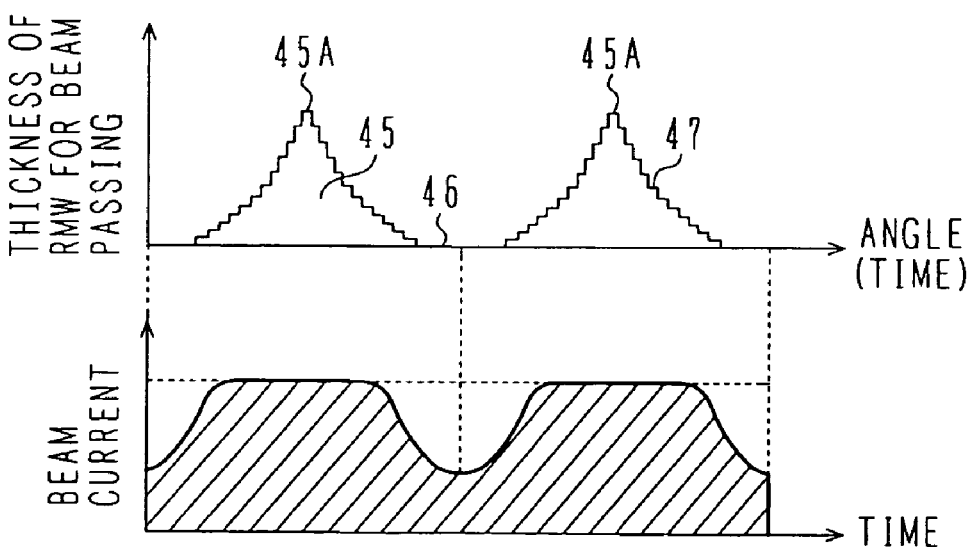
Figure 12:
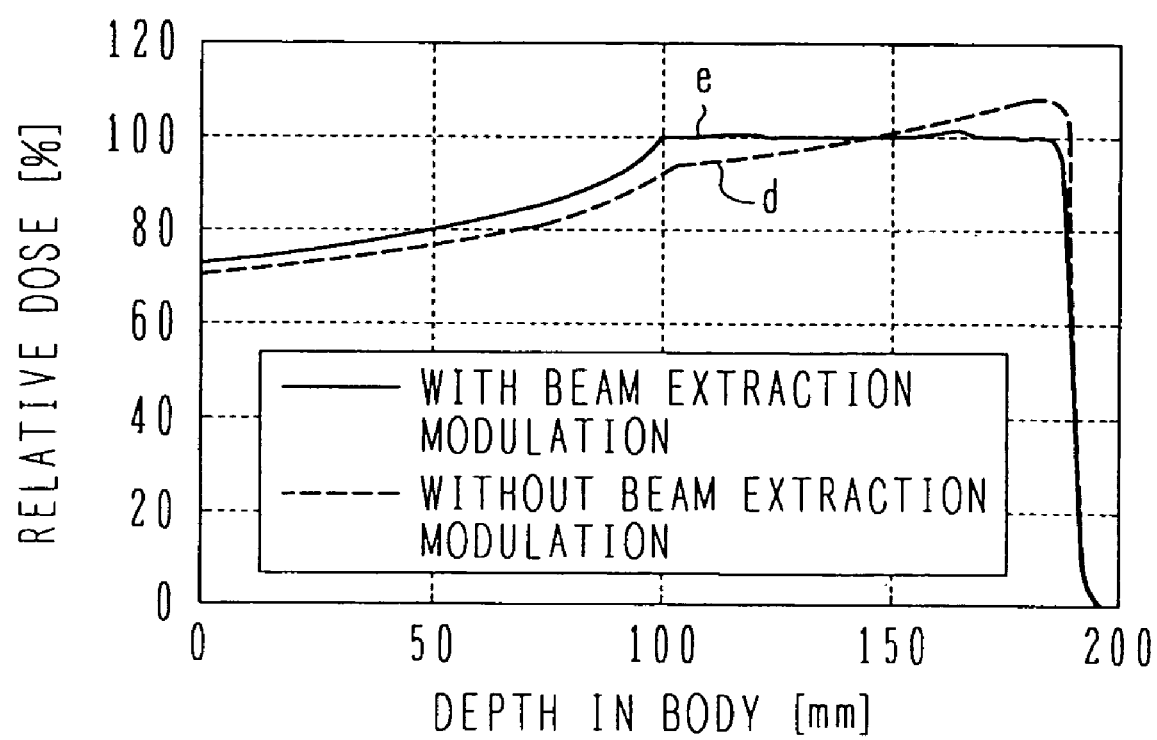
FIG. 12 illustrates a dose distribution in the beam progression direction (depth direction)

FIGS. 11 and 12 show that the dose distribution in the depth direction of the body can be adjusted to a uniform distribution by adjusting the ion beam extraction intensity on the basis of the rotational angle of the RMW 40, even when an ion beam having energy different from the energy to which the shape of the RMW 40 is optimized is incident on the RMW 40. FIG. 12 illustrates the dose distribution in the depth direction of the body when an ion beam having energy E2 that is lower than energy E1 is emitted to the RMW 40 having a shape that is optimized for energy E1. In FIG. 12, d represents the dose distribution obtained when an ion beam of energy E2 is emitted at a constant extraction intensity with respect to the rotational angle of the RMW 40 (refer to FIG. 11A), whereas e represents the dose distribution obtained when an ion beam is extracted on the basis of the information shown in FIG. 9 (refer to FIG. 11B) In the case of FIG. 11B, the intensity of the ion beam of energy E2 is reduced at the openings 46 of the RMW 40 and the flat section 47 where the thickness of the blades 45 is relatively small. In other areas, an ion beam is emitted at an intensity of 100%. Since the ion beam intensity passing through the openings 46 and the flat section 47 where the thickness of the blades 45 is relatively small is reduced, the dose of ion beam generating a Bragg peak deep inside the body is reduced. On the other hand, in the ion beam intensity passing through the flat section 47 where the thickness of the blades 45 is relatively great, the dose generating a Bragg peak near the surface of the body is relatively increased. As a result, the uniformity of the dose distribution, such as that represented by the dose distribution d, can be improved to a dose distribution, such as that represented by the dose distribution e, by reducing the dose reaching the area deep inside the body and increasing the dose at near the surface of the body.

Figure 13A:
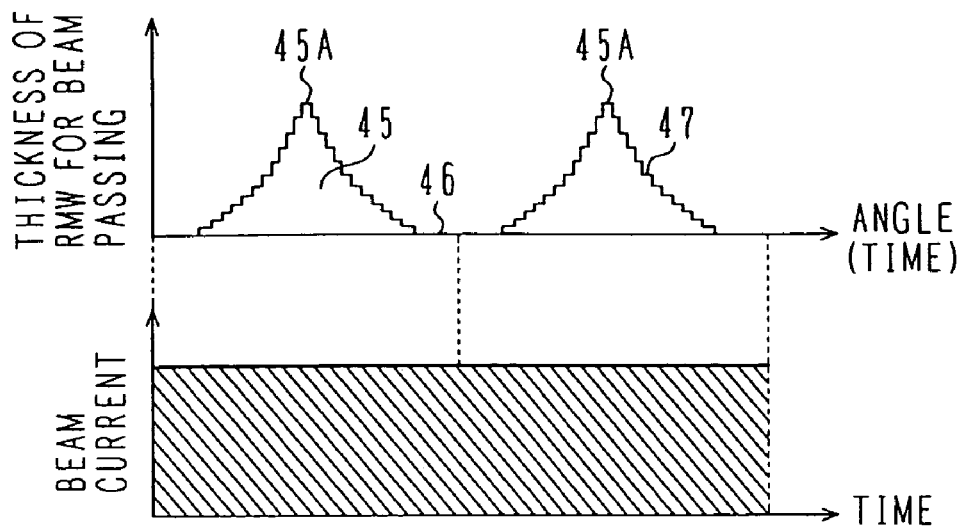
FIGS. 13A and 13B illustrate the relationship between the ion beam extraction intensity and the RMW angle, where
Figure 13B:
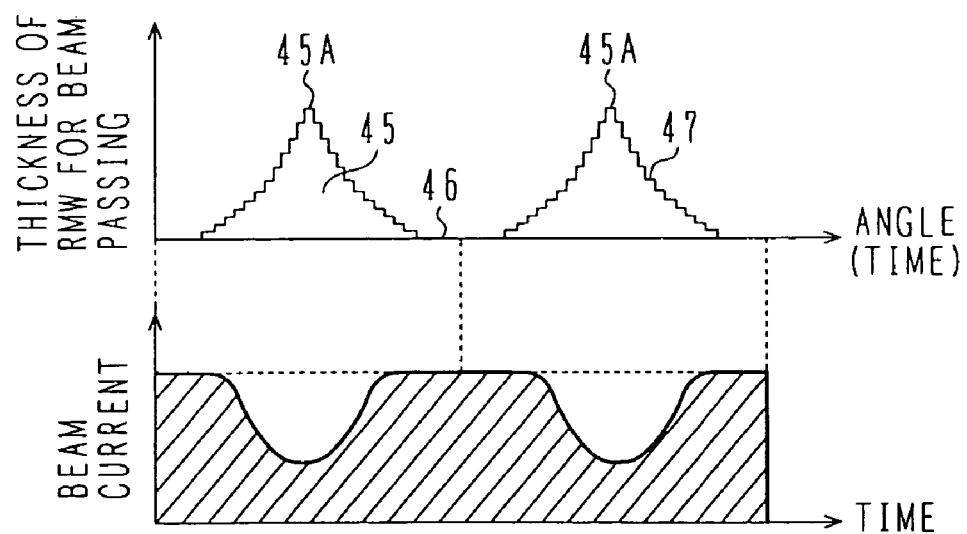
Figure 14:
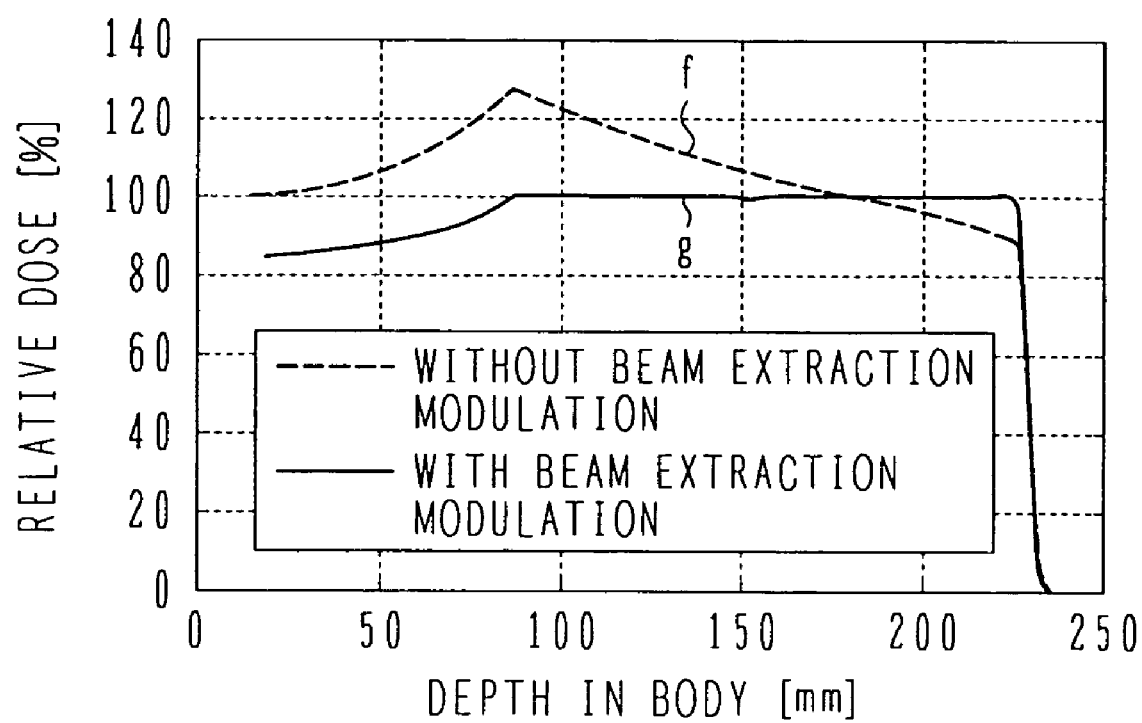
FIG. 14 illustrates a dose distribution in the beam progression direction (depth direction) when the energy of the incident beam is high.

FIGS. 13 and 14 illustrate how the dose distribution in the depth direction of the body can be adjusted to obtain a uniform distribution by adjusting the ion beam extraction intensity on the basis of the rotational angle of the RMW 40. FIG. 14 illustrates the dose distribution in the depth direction of the body when an ion beam having energy E3 that is greater than energy E1 is emitted to the RMW 40 having a shape that is optimized for the energy E1. Since the energy E3 of the ion beam is greater than the energy E1, when an ion beam of energy E2 is emitted at a constant extraction intensity with respect to the rotational angle of the RMW 40 (refer to FIG. 13A), as represented by f in FIG. 14, the dose emitted to an area deep inside the body is small, whereas the dose emitted to an area near the surface of the body is great. In such a case, as shown in FIG. 13B, the extraction intensity of the ion beam incident on the flat section 47 where the thickness of the blades 45 is relatively great is reduced, whereas the extraction intensity of the ion beam incident on other areas in the circumferential direction is normal. In this way, the dose of ion beam generating a Bragg peak near the surface of the body is reduced, where as the dose generating a Bragg peak deep inside the body is relatively increased. As a result, the uniformity of the dose distribution is improved in the dept direction, as represented by g in FIG. 14.

Since the RMW 40 is rotated and the thickness of the RMW 40 in the axial direction differs in the rotational direction, when controlling the extraction intensity of an ion beam on the basis of the rotational angle of the RMW 40 is equivalent to controlling the extraction intensity of an ion beam on the basis of the thickness of the RMW 40 in the axial direction. The beam extraction intensity controller 90 determines the thickness of the RMW 40 in the axial direction on the basis of angle information input from the RMW angle detection controller 63. The beam extraction intensity controller 90 is capable of controlling the extraction intensity of an ion beam such that the extraction intensity of the ion beam is changed when the flat sections 47 having different thicknesses in the axial direction are aligned with the beam axis m. Moreover, it is also possible to control the extraction intensity of an ion beam so that it changes while the ion beam passes through a single flat section 47.

According to this embodiment, the following advantages are achieved.

(1) According to this embodiment, the extraction intensity of an ion beam extracted from the synchrotron 4 is controlled according to the rotational angle of the RMW 40 having different thicknesses along the rotational direction. Therefore, even when an ion beam having energy different from the energy to which the shape of the RMW 40 is optimized is emitted to the RMW 40, a uniform dose distribution is obtained at the corresponding SOBP width. Consequently, the particle beam therapy system according to this embodiment is capable of reducing the number of RMWs included in the system. By reducing the number of RMWs, the frequency of replacing RMWs can be reduced. As a result, the number of patients that can be treated per year is increased. Furthermore, by reducing the number of RMWs, storage space in a medial facility required for storing RMWs can be reduced.

Figure 15A:
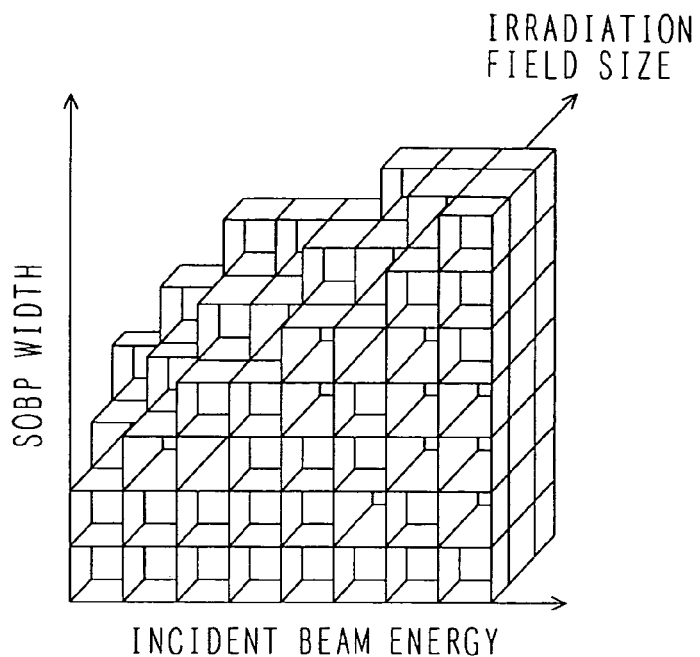
FIGS. 15A, 15B, and 15C illustrate an overview on the number of required RMWs, where
Figure 15B:
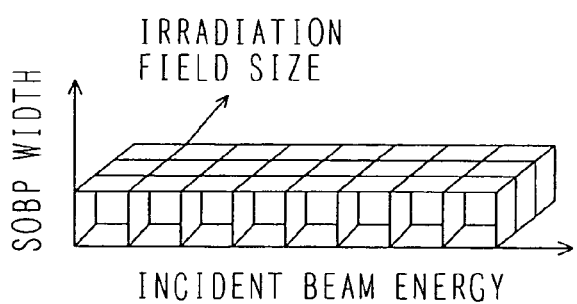
Figure 15C:
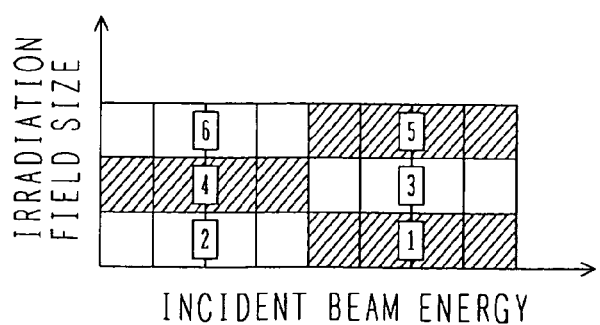

The reduction in the required number of RMWs will be described in detail below with reference to FIG. 15. The number of cubes illustrated in FIG. 15 represents the number of required RMWs. A conventional particle therapy system employing RMWs required 127 RMWs corresponding to various energy levels, SOBP widths, and irradiation field sizes of the incident ion beam (refer to FIG. 15A). As described above, by starting and stopping extraction of an ion beam according to the rotational angle of a rotating RMW, various different SOBP widths are obtained with a single RMW 40. Therefore, the number of required RMWs is significantly reduced to 24 RMWs corresponding to the different beam energy levels and SOBP widths (refer to FIG. 15B). According to this embodiment, it is possible to obtain uniform dose distributions at SOBP widths corresponding to different levels of beam energy with a single RMW. Therefore, the number of required RMWs can be further reduced to 6 to 24 RMWs, as mentioned above (refer to FIG. 15C).

(2) According to this embodiment, since the intensity of an ion beam extracted from the accelerator is controlled in accordance with the information stored in the memory (storage device) 75 of the irradiation controller 70, the control is simplified, and thus, the structure of the system can be simplified.

(3) According to this embodiment, since the thickness in the axis direction of the RMW changes along the rotational direction, the uniformity of the dose can be controlled in accordance with the intensity of the beam passing through the different steps of the RMW. In other words, even if the intensity of the beam passing through a specific area of the steps of the RMW changes, so long as the intensity of the beam passing through all of the steps is not changed, the uniformity of the dose is not affected.

(4) According to this embodiment, the extraction intensity of an ion beam is adjusted by modulating the amplitude of an RF signal supplied to the RF applying device. Therefore, a charged particle beam irradiation system capable of achieving the advantages of the present invention can be obtained by providing a beam extraction intensity controller for outputting an amplitude modulation signal and a signal combiner for outputting an RF signal for extraction having modulated amplitude to the RF applying device to the currently-operating ion beam generator. Consequently, the dose distribution in the depth direction of the body within the SOBP width can be even more uniformized without employing a complex structure.

An amplitude modulation signal may be combined with an RF signal by supplying the amplitude modulation signal to the signal combiner 92, without providing the gating switch 9. In this way, the intensity of an ion beam extracted from the synchrotron 4 can be controlled. Consequently, the above-described advantages are achieved, and the number of required RMWs can be reduced to a number lower than 127. However, more six RMWs are required.

According to this embodiment, information on the beam extraction intensity for each predetermined rotational angle (every 1° for this embodiment) is stored in the memory 75. The beam extraction intensity controller 90 constantly outputs an amplitude modulation signal based on this information to the signal combiner 92. However, the information stored in the memory 75 may be information on the rotational angle at which the beam extraction intensity is to be changed and the beam extraction intensity in respect to each irradiation pattern. In such a case, the beam extraction intensity controller 90 outputs an amplitude modulation signal to the signal combiner 92 only when the rotational angle is the rotational angle at which the beam extraction intensity is to be changed. When an amplitude modulation signal is input, the signal combiner 92 updates the amplitude modulation signal stored in a memory (not shown in the drawings) and combines the updated amplitude modulation signal and the RF signal from the RF power source 8 to generate an RF signal for extraction. The signal combiner 92 outputs this RF signal for extraction until the amplitude modulation signal is further updated. According to this method, the beam extraction intensity controller 90 outputs an amplitude modulation signal only when there is a change in the beam extraction intensity. Therefore, the frequency of outputting an amplitude modulation signal can be reduced, and beam extraction can be carried out more accurately.

According to this embodiment, the extraction intensity of an ion beam extracted from the synchrotron 4 is adjusted in a manner such that the dose distribution along the SOBP width in the beam progression direction is uniform. However, when a doctor desires to obtain a predetermined dose distribution in the beam progression direction, such as the dose distribution shown in FIG. 12D where the dose is small near the surface of the body whereas the dose is great deep inside the body, the dose distribution shown in FIG. 14*f* where the dose is great near the surface of the body whereas the dose is small deep inside the body, or a dose distribution in which the dose in a specific area within the SOBP width is small, the desired dose distribution can be obtained by changing the form of the amplitude modulation signal, as shown in FIG. 10O. Accordingly, the flexibility in extracting the charged particle beam increases.

According to this embodiment, the rotational angle of the RMW 40 is determined on the basis of the rotational angle of the rotary shaft 48 detected by the goniometer 51. However, the rotational angle of the RMW 40 can be determined on the basis of time information obtained by measuring the amount of time that elapses from the start of rotation of the RMW 40.

When an affected part K of the body of a patient 22 is irradiated with a charged particle beam, an irradiation method (i.e., cross-fire technique) in which the affected part K is irradiated with half the target dose from one direction (hereinafter this direction is referred as a "first irradiation direction" and the irradiation process is referred to as a "first irradiation"), and then after the first irradiation is completed, the affected part K of the body is irradiated with the remaining half of the target dose from another direction (hereinafter this direction is referred as a "second irradiation direction" and the irradiation process is referred to as a "second irradiation"). If the depth of the affected part K from the surface of the body of the patient 22 in the first irradiation direction differs from the depth of the affected part K from the surface of the body of the patient 22 in the second irradiation direction, the levels of the beam energy of the first irradiation and the second irradiation differ. For example, conventionally, to emit a charged particle beam having energy of 250 MeV as the first irradiation and to emit a charged particle beam having energy of 200 MeV as the second irradiation, the energy adjuster had to be changed for the first irradiation and the second irradiation. While the energy adjuster is being changed, the patient has to stay on the treatment bed for a long time. This is a great stress to the patient. According to this embodiment, since the energy adjuster does not have to be changed, less stress is placed on the patient.

Second Embodiment

A particle beam therapy system that is a charged particle beam irradiation system according to another embodiment of the present invention will be described below with reference to FIG. 16.

A proton beam therapy system according to this embodiment has the same structure as the proton beam therapy system according to the first embodiment, except that the beam extraction intensity controller 90 included in the irradiation controller 70 is replaced by a beam extraction intensity controller 90A. Moreover, the gating switch 9 is not provided and the signal combiner 92 is directly connected to the RF applying electrode 7. According to this embodiment, ion beam extraction is started and stopped without using the gating switch 9.

Figure 17A:
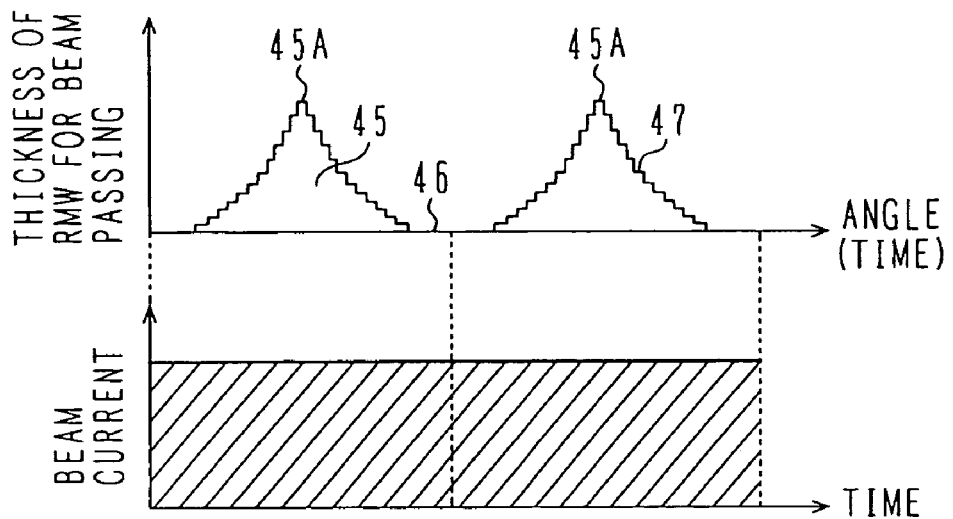
FIGS. 17A and 17B illustrate the relationship between the ion beam extraction intensity and the RMW angle, where
Figure 17B:
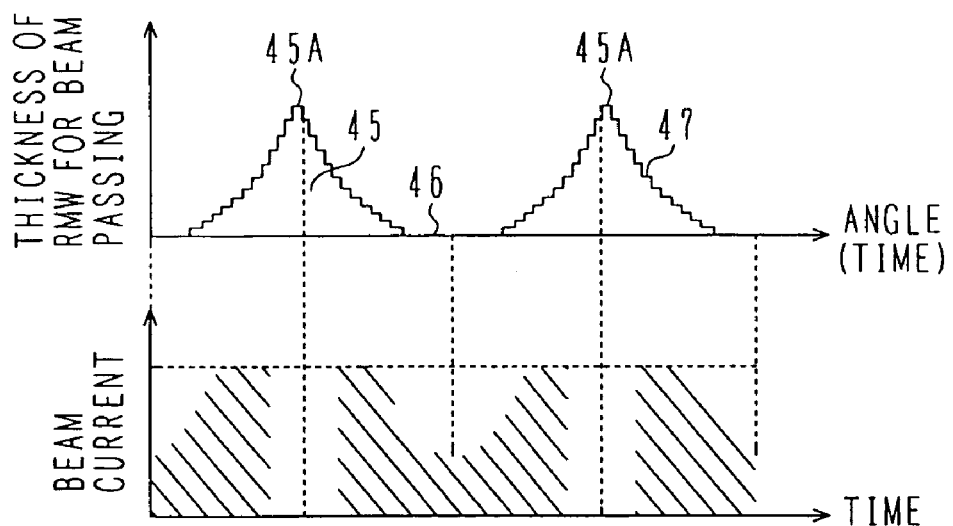

The beam extraction intensity controller 90A outputs a control signal obtained by combining a beam extraction ON/OFF signal (refer to FIG. 16U) and an amplitude modulation signal (FIG. 16O) to the signal combiner 92. The signal combiner 92 combines an RF signal (FIG. 16P) and the control signal so as to output an RF signal for extraction (refer to FIG. 16R) that includes a beam extraction start signal and a beam extraction stop signal and that has modulated amplitude. The RF applying electrode 7 applies this RF signal for extraction to an ion beam to change the intensity of the ion beam extracted from the synchrotron 4, as shown in FIGS. 16S and 17B. The change in the intensity of the ion beam is the same as that in the first embodiment.

Figure 18:
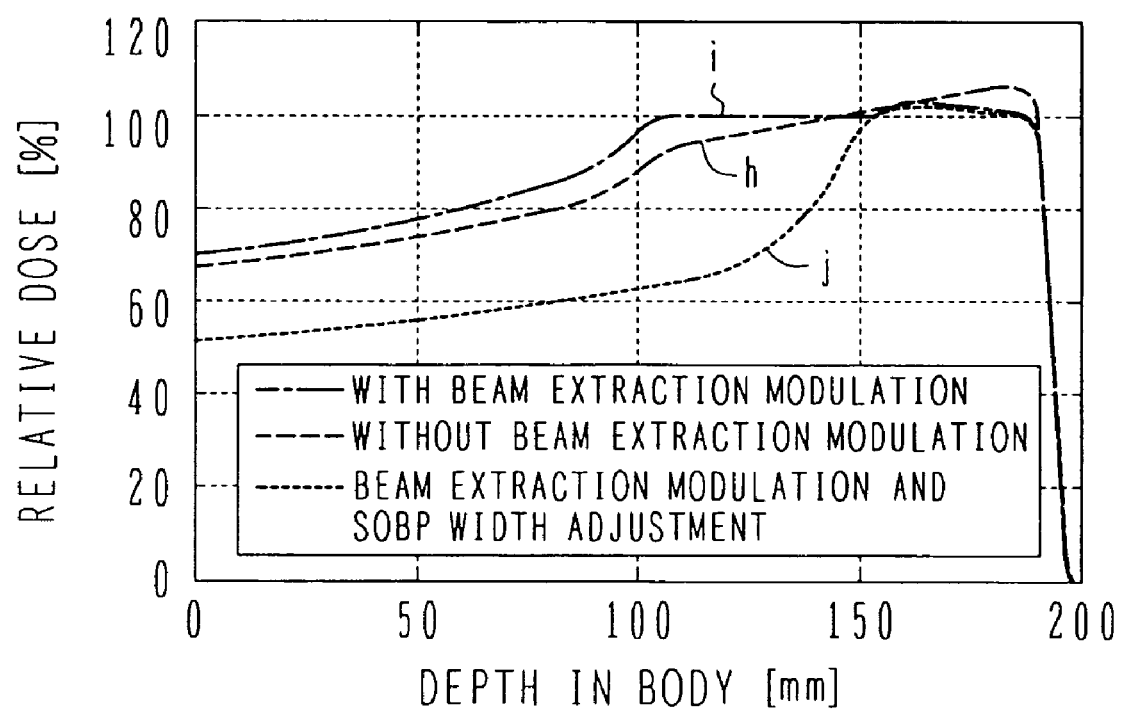
FIG. 18 illustrates a dose distribution in the beam progression direction (depth direction)

According to this embodiment, when the signal combiner 92 receives a control signal including a beam extraction ON/OFF signal, ion beam extraction is started by the ON set value and ion beam extraction is stopped by the OFF set value so as to obtain a predetermined SOBP width in the same manner as in the first embodiment. According to this embodiment, the extraction intensity of an ion beam can be controlled, and, as represented by i and j in FIG. 18, the dose distribution in the depth direction can be uniformized. In FIG. 18, h represents the dose distribution obtained when an ion beam of a predetermined extraction intensity is constantly emitted at any rotational angle of the RMW 40; i represents the dose distribution obtained when an ion beam is emitted according to the rotational angle of the RMW 40 such that the extraction intensity is small at the openings 46 and the flat sections 47, where the thickness of the blades 45 is relatively small, and is normal in other areas in the circumferential direction; j represents the dose distribution obtained when an ion beam is emitted according to the rotational angle of the RMW 40 such that the extraction intensity is small at the openings 46 and the flat sections 47, where the thickness of the blades 45 is relatively small, is normal in other areas in the circumferential direction, and is stopped while the flat sections 47, where the thickness of the blades 45 is relatively great, passes across the beam axis.

According to this embodiment, the same advantages as the above-described advantages (1) to (4) achieved by the first embodiment can be achieved.

Third Embodiment

Figure 19:
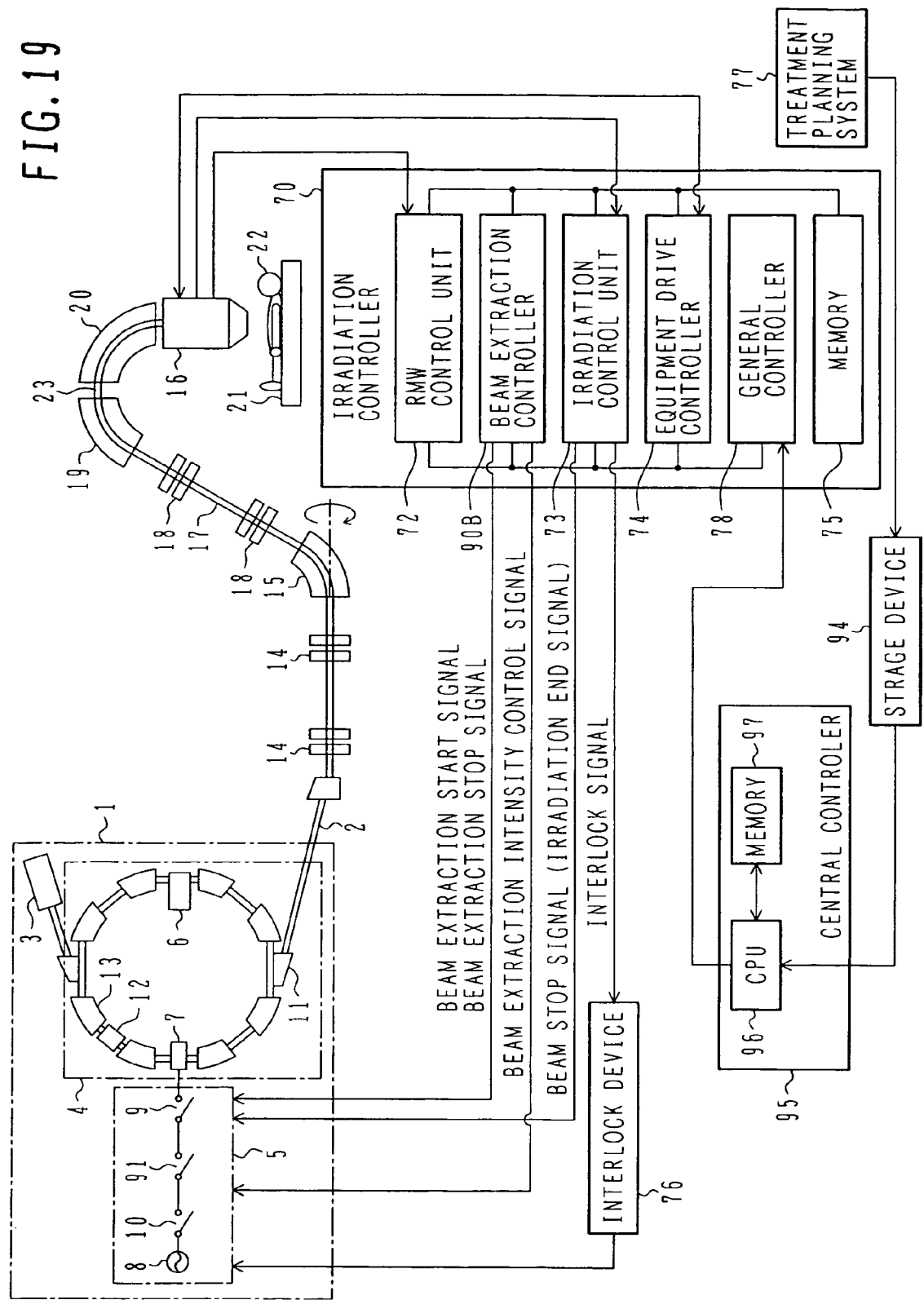
FIG. 19 is a schematic view of the overall structure of a particle beam therapy system according to another preferred embodiment of the present invention.

A particle beam therapy system that is a charged particle beam irradiation system according to another embodiment of the present invention will be described below with reference to FIG. 19. A proton beam therapy system according to this embodiment has the same structure as that of the proton beam therapy system according to the first embodiment, except that the signal combiner 92 is replaced by a gating switch 91. According to this embodiment, a memory 75B stores the information shown in FIGS. 7, 8, and 20.

As shown in FIG. 20, the memory 75B stores information on the relationship between the rotational angle set value of the RMW 40 and the beam extraction pattern. As shown in FIG. 20, if the beam extraction pattern is determined, the ion beam extraction intensity corresponding to the rotational angle of the RMW 40 can be determined. According to the first embodiment, the extraction intensity of the ion beam extracted from the synchrotron 4 is controlled in an analog manner (0% to 100%). The particle beam therapy system according to this embodiment controls the extraction intensity of the ion beam extracted from the synchrotron 4 according to the rotational angel of the RMW 40 of 0% or 100% (in FIG. 20, "1" represents a beam extraction intensity of 100%, whereas "0" represents a beam extraction intensity of 0%). In this way, even when an ion beam having an energy level different from the energy level to which the shape of the RMW 40 is optimized is emitted to the RMW 40, a uniform dose distribution is obtained within the SOBP width of the SOBP generated inside the body in the beam progression direction. Control according to this embodiment by a beam extraction intensity controller 90B having this function will be described in detail below.

The general control unit 78 outputs treatment plan information to the beam extraction intensity controller 90B. The beam extraction intensity controller 90B selects information on the RMW type (for example, 1-B) and information on the beam extraction pattern (for example, 1-B-I) from the information stored in the memory 75B, as shown in FIG. 7, on the basis of irradiation field diameter, range, and beam energy. The beam extraction intensity controller 90B also selects an ON set value and an OFF set value from information on SOBP width and RMW type and a beam extraction intensity set value (0% or 100%) corresponding to the rotational angles from the information stored in the memory 75B, as shown in FIG. 20, according to the beam extraction pattern (1-B-I).

Figure 21:
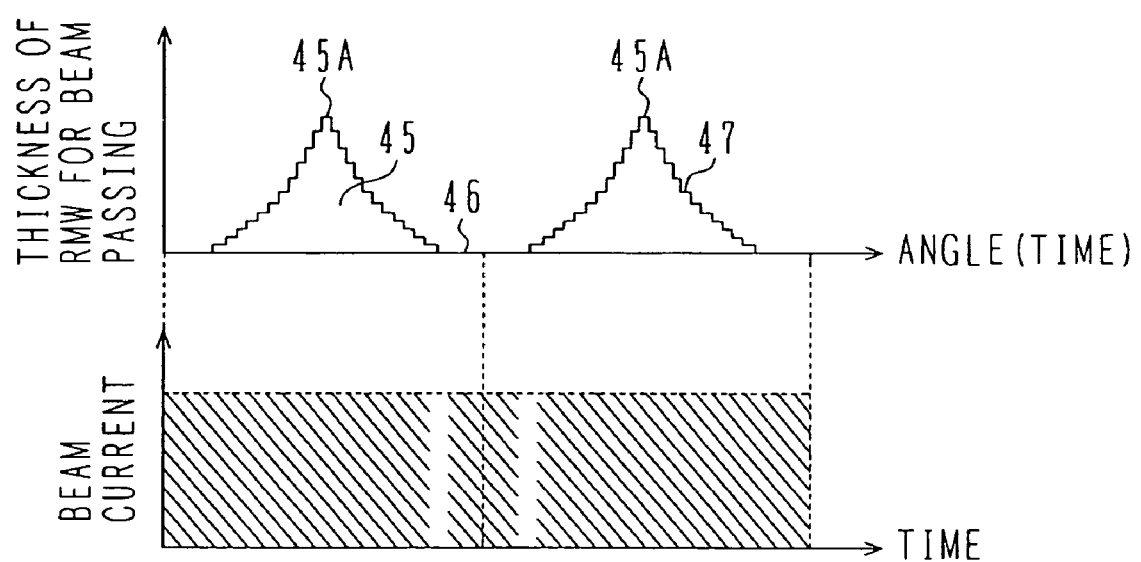
FIG. 21 illustrates the relationship between the ion extraction intensity and the RMW rotational angle when the beam extraction intensity is controlled by starting and stopping beam extraction.

The beam extraction intensity controller 90B controls the extraction intensity of the ion beam from the synchrotron 4 on the basis of the beam extraction intensity set value corresponding to the input rotational angle information value. In other words, the beam extraction intensity controller 90B generates an ion beam extraction intensity control signal according to the extraction intensity set value of the ion beam from the memory 75B and outputs this generated signal to the gating switch 91. The gating switch 91 closes when it receives a beam extraction intensity control signal corresponding to a beam extraction intensity of 100%, whereas it opens when it receives a beam extraction intensity control signal corresponding to a beam extraction intensity of 0%. An RF signal sent from the RF power source 8 is input to the gating switch 91 via the gating switch 10. According to this embodiment, as shown in FIG. 21, the beam is extracted in such a manner that there is a plurality of ion beam extraction termination periods in short pulses.

When an ion beam of energy E2 that is smaller than energy E1 is emitted at the RMW 40 having a shape optimized for the energy E1, the openings 46 and the flat sections 47 where the blades 45 have a relatively small thickness is irradiated with a pulsed ion beam having extraction termination periods with respect to the rotational angle of the RMW 40, and the other areas in the circumferential direction are irradiated with an ion beam intensity of 100%. In this way, the dose distribution for the SOBP width in the depth direction of the body is uniformized. When an ion beam of energy E3 that is greater than energy E1 is emitted at the RMW 40 having a shape optimized for the energy E1, the flat sections 47 where the blades 45 have a relatively great thickness is irradiated with a pulsed ion beam having extraction termination periods with respect to the rotational angle of the RMW 40, and the other areas in the circumferential direction are irradiated with normal ion beam intensity. In this way, the dose distribution in the depth direction of the body is uniformized.

According to this embodiment, the same advantages as the above-described advantages (1) to (3) achieved by the first embodiment can be achieved. In addition, the following advantage is achieved.

(5) According to this embodiment, since the extraction intensity of the ion beam extracted from the synchrotron is controlled so that it is 0% or 100%, the system is simplified.

What is claimed is:

1. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and having passed said beam energy modulator, the beam energy modulator being rotated and a thickness thereof in an axial direction differing in a rotational direction; and
a controller for controlling the extraction intensity of the charged particle beam extracted from the synchrotron by controlling an amplitude of a radio frequency signal supplied to the radio frequency applying device on the basis of a rotational angle of the beam energy modulator in the rotational direction, the extraction intensity being controlled to vary among different levels on the basis of the rotational angle of the beam energy modulator during a period after a start of the extraction of the charged particle beam and before a stop of the extraction of the charged particle beam while the charged particle beam is being extracted.

2. The charged particle beam irradiation system according to claim 1, further comprising:
an angle detector for detecting the rotational angle of the beam energy modulator,
wherein the controller controls the extraction intensity of the charged particle beam extracted from the synchrotron on the basis of the rotational angle detected by the angle detector.

3. The charged particle beam irradiation system according to claim 1, further comprising:
a storage device for storing a plurality of extraction intensity set values of charged particle beams extracted from the synchrotron, the extraction intensity set values corresponding to a plurality of rotational angles of the beam energy modulator,
wherein the controller controls the extraction intensity of the charged particle beam on the basis of one of the extraction intensity set values selected from the storage device according to the rotational angle of the beam energy modulator.

4. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and having passed said beam energy modulator, the beam energy modulator being rotated and a thickness thereof in an axial direction differing in a rotational direction; and
a controller for controlling the amplitude of a radio frequency signal supplied to the radio frequency applying device on the basis of a rotational angle of the beam energy modulator in the rotational direction, the amplitude being controlled to vary among different levels on the basis of the rotational angle of the beam energy modulator during a period after a start of the extraction of the charged particle beam and before a stop of the extraction of the charged particle beam while the charged particle beam is being extracted.

5. The charged particle beam irradiation system according to claim 4, further comprising:

an angle detector for detecting the rotational angle of the beam energy modulator, wherein the controller controls the amplitude of the radio frequency signal on the basis of the rotational angle detected by the angle detector.

6. The charged particle beam irradiation system according to claim 1, wherein the thickness of the beam energy modulator in the axial direction changes in the rotational direction due to a structure provided with a plurality of steps.

7. The charged particle beam irradiation system according to claim 1, wherein the beam energy modulator includes a blade, the thickness of the blade in the axial direction differing in the rotational direction.

8. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and having passed said beam energy modulator, the beam energy modulator being rotated and a thickness thereof in an axial direction differing in a rotational direction; and
a controller for controlling the extraction intensity of the charged particle beam extracted from the synchrotron by controlling an amplitude of a radio frequency signal supplied to the radio frequency applying device on the basis of the thickness of the beam energy modulator in the axial direction, the extraction intensity being controlled to vary among different levels on the basis of the thickness of the beam energy modulator during a period after a start of the extraction of the charged particle beam and before a stop of the extraction of the charged particle beam while the charged particle beam is being extracted.

9. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and having passed said beam energy modulator, the beam energy modulator being rotated and a thickness thereof in an axial direction differing in a rotational direction; and
a controller for controlling the amplitude of a radio frequency signal supplied to the radio frequency applying device on the basis of the thickness of the beam energy modulator in the axial direction, the amplitude being controlled to vary among different levels on the basis of the thickness of the beam energy modulator during a period after a start of the extraction of the charged particle beam and before a stop of the extraction of the charged particle beam while the charged particle beam is being extracted.

10. The charged particle beam irradiation system according to claim 8, wherein the thickness of the beam energy modulator is determined on the basis of the rotational angle of the beam energy modulator.

11. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and having passed said beam energy modulator, the beam energy modulator being rotated and a thickness thereof in an axial direction differing in a rotational direction; and
a controller for controlling the extraction intensity of the charged particle beam extracted from the synchrotron while the charged particle beam is being extracted, when an ion beam having energy different from the energy to which the shape of the beam energy modulator is optimized is incident on the beam energy modulator, the extraction intensity being controlled to vary among different levels by controlling an amplitude of a radio frequency signal supplied to the radio frequency applying device synchrotron on the basis of one of the rotational angle in the rotational direction or the thickness in the axial direction of the beam energy modulator during a period after a start of the extraction of the charged particle beam and before a stop of the extraction of the charged particle beam while the charged particle beam is being extracted.

12. The charged particle beam irradiation system according to claim 1, wherein the controller further controls the period for extracting the charged particle beam by starting and stopping the beam extraction on the basis of the rotational angle of the beam energy modulator.

13. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and having passed said beam energy modulator, the beam energy modulator being rotated and a thickness thereof in an axial direction differing in a rotational direction; and
a controller for outputting an extraction start signal and an extraction stop signal for starting and stopping the extraction of a charged particle beam orbiting the synchrotron and a control signal for controlling the extraction intensity of the charged particle beam extracted from the synchrotron by controlling an amplitude of a radio frequency signal supplied to the radio frequency applying device on the basis of the rotational angle of the beam energy modulator in the rotational direction, the extraction intensity being controlled to vary among different levels on the basis of the rotational angle of the beam energy modulator during a period after a start of the extraction of the charged particle beam and before a stop of the extraction of the charged particle beam while the charged particle beam is being extracted.

14. The charged particle beam irradiation system according to claim 7, wherein, when an ion beam having energy that is lower than the energy to which the shape of the beam energy modulator is optimized is transmitted to pass though the beam energy modulator, the controller reduces the extraction intensity of the ion beam passing through an area where the blade thickness is small compared to the extraction intensity of the ion beam passing through other areas.

15. The charged particle beam irradiation system according to claim 7, wherein, when an ion beam having energy that is higher than the energy to which the shape of the beam energy modulator is optimized is transmitted to pass through the beam energy modulator, the controller reduces the extraction intensity of the ion beam passing through a flat section of the blade of the beam energy modulator where the thickness is small compared to the extraction intensity of the ion beam passing through a flat section of the blade of the beam energy modulator where the thickness is great.

16. A method of extracting a charged particle beam, comprising the steps of:
accelerating a charged particle beam using a synchrotron, the synchrotron including a radio frequency applying device for beam extraction;
transmitting the charged particle beam extracted from the synchrotron to pass a rotating beam energy modulator, a thickness of the beam energy modulator in an axial direction differing in a rotational direction; and
controlling the extraction intensity of the charged particle beam extracted from the synchrotron by controlling an amplitude of a radio frequency signal supplied to the radio frequency applying device on the basis of the rotational angle of the beam energy modulator in the rotational direction, the extraction intensity being controlled to vary among different levels on the basis of the rotational angle of the beam energy modulator during a period after a start of the extraction of the charged particle beam and before a stop of the extraction of the charged particle beam while the charged particle beam is being extracted.

17. A method of extracting a charged particle beam, comprising the steps of:
accelerating a charged particle beam with a synchrotron, the synchrotron including a radio frequency applying device the beam extraction;
transmitting the charged particle beam extracted from the synchrotron to pass a rotating beam energy modulator, a thickness of the beam energy modulator in an axial direction differing in a rotational direction; and
controlling the extraction intensity of the charged particle beam extracted from the synchrotron by controlling an amplitude of a radio frequency signal supplied to the radio frequency applying device on the basis of a rotating time of the beam energy modulator in the rotational direction, the extraction intensity being controlled to vary among different levels on the basis of the rotating time of the beam energy modulator during a period after a start of the extraction of the charged particle beam and before a stop of the extraction of the charged particle beam while the charged particle beam is being extracted.

18. A method of extracting a charged particle beam, comprising the steps of:
accelerating a charged particle beam with a synchrotron;
modulating the amplitude of a radio frequency signal applied to a charged particle beam on the basis of a rotational angle of a beam energy modulator in a rotational direction while the charged particle beam is being extracted, the amplitude being modulated to vary among different levels on the basis of the rotational angle of the beam energy modulator during a period after a start of the extraction of the charged particle beam and before a stop of the extraction of the charged particle beam while the charged particle beam is being extracted;
applying the modulated radio frequency signal for extracting the charged particle beam from the accelerator; and
transmitting the extracted charged particle beam to pass a rotating beam energy modulator, the thickness of the beam energy modulator in an axial direction differing in the rotational direction.

19. The method of extracting a charged particle beam according to claim 16, wherein the charged particle beam is extracted from the synchrotron on the basis of extraction intensity set values of charged particle beams corresponding to a plurality of rotational angles of the beam energy modulator.

20. The method of extracting a charged particle beam according to claim 16, wherein the extraction intensity of the charged particle beam extracted from the synchrotron is further controlled by starting and stopping beam extraction.

21. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and transported through the beam irradiation apparatus along a beam axis and having passed said beam energy modulator, the beam energy modulator being rotated in a rotational direction around an axis of rotation extending in a direction along said beam axis and a thickness thereof in the axial direction differing in the rotational direction; and
a controller for controlling the extraction intensity of the charged particle beam extracted from the synchrotron by controlling an amplitude of a radio frequency signal supplied to the radio frequency applying device on the basis of a rotational angle of the beam energy modulator in the rotational direction, the extraction intensity being controlled to vary among different levels on the basis of the rotational angle of the beam energy modulator during a period after a start of the extraction of the charged particle beam and before a stop of the extraction of the charged particle beam while the charged particle beam is being extracted.

22. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and having passed said beam energy modulator, the beam energy modulator being rotated and the thickness thereof in the axial direction differing in the rotational direction, the beam energy modulator being used to control a width of a spread-out Bragg peak (SOBP); and
a controller for controlling the extraction intensity of the charged particle beam extracted from the synchrotron by controlling an amplitude of a radio frequency signal supplied to the radio frequency applying device on the basis of the rotational angle of the beam energy modulator, the extraction intensity being controlled while the charged particle beam is being extracted from the synchrotron before reaching the beam irradiation apparatus.

23. The charged particle beam irradiation system according to claim 22, further comprising:
an angle detector for detecting the rotational angle of the beam energy modulator,
wherein the controller controls the extraction intensity of the charged particle beam extracted from the synchrotron on the basis of the rotational angle detected by the angle detector.

24. A charged particle beam irradiation system comprising:
an ion source for generating a charged particle beam;
a synchrotron for accelerating the charged particle beam extracted from the ion source, the synchrotron including a radio frequency applying device for beam extraction;

a beam irradiation apparatus having a beam energy modulator and arranged for irradiating an object with the charged particle beam extracted from said synchrotron and having passed said beam energy modulator, the beam energy modulator being rotated and the thickness thereof in the axial direction differing in the rotational direction, the beam energy modulator being used to control a width of a spread-out Bragg peak (SOBP); and a controller for controlling the extraction intensity of the charged particle beam extracted from the synchrotron by controlling an amplitude of a radio frequency signal supplied to the a radio frequency applying device on the basis of the rotational angle of the beam energy modulator, the extraction intensity being controlled while the charged particle beam is being extracted from the synchrotron before reaching the beam irradiation apparatus.

25. The charged particle beam irradiation system according to claim 22, further comprising:

a storage device for storing a plurality of extraction intensity set values of charged particle beams extracted from the synchrotron, the extraction intensity set values corresponding to a plurality of rotational angles of the beam energy modulator, wherein the controller controls the extraction intensity of the charged particle beam on the basis of one of the extraction intensity set values selected from the storage device according to the rotational angle of the beam energy modulator.

26. A charged particle beam irradiation system comprising:

a synchrotron for accelerating a charged particle beam, the synchrotron including a radio frequency applying device for beam extraction;

a beam irradiation apparatus having a beam energy modulator and arranged for irradiating an object with the charged particle beam extracted from said synchrotron and having passed said beam energy modulator, the beam energy modulator being rotated and the thickness thereof in the axial direction differing in the rotational direction, the beam energy modulator being used to control a width of a spread-out Bragg peak (SOBP); and a controller for controlling the amplitude of a radio frequency signal supplied to the radio frequency applying device on the basis of the rotational angle of the beam energy modulator, the amplitude being controlled while the charged particle beam is being extracted from the synchrotron before reaching the beam irradiation apparatus.

27. The charged particle beam irradiation system according to claim 26, further comprising:

an angle detector for detecting the rotational angle of the beam energy modulator, wherein the controller controls the amplitude of the radio frequency signal on the basis of the rotational angle detected by the angle detector.

28. The charged particle beam irradiation system according to claim 22, wherein the thickness of the beam energy modulator in the axial direction changes in the rotational direction due to a structure provided with a plurality of steps.

29. The charged particle beam irradiation system according to claim 22, wherein the beam energy modulator includes a blade, the thickness of the blade in the axial direction differing in the rotational direction.

30. A charged particle beam irradiation system comprising:

a synchrotron for accelerating a charged particle beam, the synchrotron including a radio frequency applying device for beam extraction;

a beam irradiation apparatus having a beam energy modulator and arranged for irradiating an object with the charged particle beam extracted from said synchrotron and having passed said beam energy modulator, the beam energy modulator being rotated and the thickness thereof in the axial direction differing in the rotational direction, the beam energy modulator being used to control a width of a spread-out Bragg peak (SOBP); and a controller for controlling the extraction intensity of the charged particle beam extracted from the synchrotron by controlling an amplitude of a radio frequency signal supplied to the radio frequency applying device on the basis of the thickness of the beam energy modulator in the axial direction, the extraction intensity being controlled while the charged particle beam is being extracted from the synchrotron before reaching the beam irradiation apparatus.

31. A charged particle beam irradiation system comprising:

a synchrotron for accelerating a charged particle beam, the synchrotron including a radio frequency applying device for beam extraction;

a beam irradiation apparatus having a beam energy modulator and arranged for irradiating an object with the charged particle beam extracted from said synchrotron and having passed said beam energy modulator, the beam energy modulator being rotated and the thickness thereof in the axial direction differing in the rotational direction, the beam energy modulator being used to control a width of a spread-out Bragg peak (SOBP); and a controller for controlling the amplitude of a radio frequency signal supplied to the radio frequency applying device on the basis of the thickness of the beam energy modulator in the axial direction, the amplitude being controlled while the charged particle beam is being extracted from the synchrotron before reaching the beam irradiation apparatus.

32. The charged particle beam irradiation system according to claim 30, wherein the thickness of the beam energy modulator is determined on the basis of the rotational angle of the beam energy modulator.

33. A charged particle beam irradiation system comprising:

a synchrotron for accelerating a charged particle beam, the synchrotron including a radio frequency applying device for beam extraction;

a beam irradiation apparatus having a beam energy modulator and arranged for irradiating an object with the charged particle beam extracted from said synchrotron and having passed said beam energy modulator, the beam energy modulator being rotated and the thickness thereof in the axial direction differing in the rotational direction, the beam energy modulator being used to control a width of a spread-out Bragg peak (SOBP); and a controller for controlling the extraction intensity of the charged particle beam extracted from the synchrotron while the charged particle beam is being extracted from the synchrotron before reaching the beam irradiation apparatus, by controlling an amplitude of a radio frequency signal supplied to the radio frequency applying device when an ion beam having energy different from the energy to which the shape of the beam energy modulator is optimized is incident on the beam energy modulator.

34. The charged particle beam irradiation system according to claim 22, wherein the controller controls the period for extracting the charged particle beam by starting and stopping the beam extraction on the basis of the rotational angle of the beam energy modulator.

35. A charged particle beam irradiation system comprising:
a synchrotron for accelerating a charged particle beam, the synchrotron including a radio frequency applying device for beam extraction;
a beam irradiation apparatus having a beam energy modulator and arranged for irradiating an object with the charged particle beam extracted from said synchrotron and having passed said beam energy modulator, the beam energy modulator being rotated and the thickness thereof in the axial direction differing in the rotational direction; and
by controlling an amplitude of a signal supplied to the accelerator an extraction start signal and an extraction stop signal for starting and stopping the extraction of a charged particle beam orbiting the synchrotron and a control signal for controlling the extraction intensity of the charged particle beam extracted from the synchrotron before reaching the beam irradiation apparatus by controlling an amplitude of a radio frequency signal supplied to the radio frequency applying device on the basis of the rotational angle of the beam energy modulator.

36. The charged particle beam irradiation system according to claim 29, wherein, when an ion beam having energy that is lower than the energy to which the shape of the beam energy modulator is optimized is transmitted to pass though the beam energy modulator, the controller reduces the extraction intensity of the ion beam passing through an area where the blade thickness is small compared to the extraction intensity of the ion beam passing through other areas.

37. The charged particle beam irradiation system according to claim 29, wherein, when an ion beam having energy that is higher than the energy to which the shape of the beam energy modulator is optimized is transmitted to pass through the beam energy modulator, the controller reduces the extraction intensity of the ion beam passing through a flat section of the blade of the beam energy modulator where the thickness is small compared to the extraction intensity of the ion beam passing through a flat section of the blade of the beam energy modulator where the thickness is great.

38. A method of extracting a charged particle beam, comprising the steps of:
accelerating a charged particle beam with a synchrotron, the synchrotron including a radio frequency applying device for beam extraction;
transmitting the charged particle beam extracted from the synchrotron to pass a rotating beam energy modulator, the thickness of the beam energy modulator in the axial direction differing in the rotational direction, the beam energy modulator being used to control a width of a spread-out Bragg peak (SOBP); and
controlling the extraction intensity of the charged particle beam extracted from the synchrotron by controlling an amplitude of a radio frequency signal supplied to the radio frequency applying device on the basis of the rotational angle of the beam energy modulator, the extraction intensity being controlled while the charged particle beam is being extracted from the synchrotron before reaching the beam energy modulator.

39. A method of extracting a charged particle beam, comprising the steps of:
accelerating a charged particle beam with a synchrotron, the synchrotron including a radio frequency applying device for beam extraction;
transmitting the charged particle beam extracted from the synchrotron to pass a rotating beam energy modulator, the thickness of the beam energy modulator in the axial direction differing in the rotational direction, the beam energy modulator being used to control a width of a spread-out Bragg peak (SOBP); and
controlling the extraction intensity of the charged particle beam extracted from the synchrotron by controlling an amplitude of a radio frequency signal supplied to the radio frequency applying device on the basis of the rotating time of the beam energy modulator, the extraction intensity being controlled while the charged particle beam is being extracted from the synchrotron before reaching the beam irradiation apparatus.

40. A method of extracting a charged particle beam, comprising the steps of:
accelerating a charged particle beam with a synchrotron;
modulating the amplitude of a radio frequency signal applied to a charged particle beam on the basis of the rotational angle of a beam energy modulator while the charged particle beam is being extracted from the synchrotron before reaching the beam irradiation apparatus;
applying the modulated radio frequency signal for extracting the charged particle beam from the synchrotron; and
transmitting the extracted charged particle beam to pass a rotating beam energy modulator, the thickness of the beam energy modulator in the axial direction differing in the rotational direction, the beam energy modulator being used to control a width of a spread-out Bragg peak (SOBP).

41. The method of extracting a charged particle beam according to claim 38, wherein the charged particle beam is extracted from the synchrotron on the basis of extraction intensity set values of charged particle beams corresponding to a plurality of rotational angles of the beam energy modulator.

42. The method of extracting a charged particle beam according to claim 38, wherein the extraction intensity of the charged particle beam extracted from the synchrotron is controlled by starting and stopping beam extraction.

* * * * *